(12) United States Patent
Tian et al.

(10) Patent No.: US 11,891,449 B2
(45) Date of Patent: Feb. 6, 2024

(54) RECOMBINANT FUSION PROTEINS TARGETING CD47 AND CD24, PREPARATION AND USE THEREOF

(71) Applicant: Immuneonco Biopharmaceuticals (Shanghai) Inc., Shanghai (CN)

(72) Inventors: Wenzhi Tian, Shanghai (CN); Song Li, Shanghai (CN); Dianze Chen, Shanghai (CN)

(73) Assignee: IMMUNEONCO BIOPHARMACEUTICALS (SHANGHAI) INC., Shanghai (CN)

( * ) Notice: Subject to any disclaimer, the term of this patent is extended or adjusted under 35 U.S.C. 154(b) by 44 days.

(21) Appl. No.: 17/543,033

(22) Filed: Dec. 6, 2021

(65) Prior Publication Data

US 2023/0114491 A1    Apr. 13, 2023

(30) Foreign Application Priority Data

Oct. 13, 2021    (CN) .......................... 202111195248.4

(51) Int. Cl.
*C07K 16/28* (2006.01)
*A61P 35/02* (2006.01)

(52) U.S. Cl.
CPC .......... *C07K 16/2896* (2013.01); *A61P 35/02* (2018.01); *C07K 2317/24* (2013.01); *C07K 2317/66* (2013.01); *C07K 2317/732* (2013.01); *C07K 2317/92* (2013.01)

(58) Field of Classification Search
CPC ............ C07K 16/2896; C07K 2317/24; C07K 2317/66; C07K 2317/732; C07K 2317/92; C07K 14/70503; C07K 2317/73; C07K 2317/76; C07K 2319/00; C07K 2319/30; C07K 14/00; C07K 2317/52; C07K 2317/56; A61P 35/02; A61P 35/00; A61K 2039/507
See application file for complete search history.

(56) References Cited

U.S. PATENT DOCUMENTS

2019/0125834 A1* 5/2019 Tian ....................... C12N 15/70
2020/0048364 A1    2/2020 Tian et al.

FOREIGN PATENT DOCUMENTS

| CN | 108623689 A | 10/2018 | |
|---|---|---|---|
| CN | 109897111 A | 6/2019 | |
| CN | 111278865 A | 6/2020 | |
| CN | 112533954 A | 3/2021 | |
| CN | 112646043 A | 4/2021 | |
| CN | 113831412 A | 12/2021 | |
| CN | 113956363 A | 1/2022 | |
| WO | 2020102422 A1 | 5/2020 | |
| WO | 2020198353 A1 | 10/2020 | |
| WO | 2020261280 A1 | 12/2020 | |
| WO | WO-2020261280 A1 * | 12/2020 | .............. A61P 35/00 |

OTHER PUBLICATIONS

Barkal et. al. Nature. 572:392-396 (2019) (Year: 2019).*
JPO, Non-Final Office Action of counterpart application JP2021-195587, dated May 23, 2023.
ISA/CN, International Search Report & Written Opinion of the International Searching Authority of corresponding application PCT/CN2022/116315, dated Nov. 25, 2022.
Wu, H et al., Prospects of antibodies targeting CD47 or CD24 in the treatment of glioblastoma, CNS Neuroscience & Therapeutics Sep. 16, 2021(Sep. 16, 2021) vol. 27 No. 10, pp. 1105-1117.
Siret Tahk et al., Evaluation of a Bifunctional Sirpα-CD123 Fusion Antibody for the Elimination of Acute Myeloid Leukemia Stem Cells, Blood Nov. 13, 2019(Nov. 13, 2019) vol. 134, Suppl. 1:2544.
JPO, Non-Final Office Action of counterpart application JP2021-195587 dated Jan. 10, 2023.

* cited by examiner

*Primary Examiner* — Julie Wu
*Assistant Examiner* — Francesca Edgingtongiordan
(74) *Attorney, Agent, or Firm* — Duane Morris LLP; Thomas J. Kowalski; Deborah L. Lu

(57) ABSTRACT

The present application provides a recombinant fusion protein containing an anti-CD24 antibody or an antibody fragment thereof, with at least one paratope of the anti-CD24 antibody or antibody fragment thereof linked via a linker to an extracellular Ig-like domain of a signal-regulatory protein (SIRP) at N-terminus of a heavy chain or a light chain constituting that paratope, wherein the recombinant fusion protein can bind to CD47, CD24 and FcR simultaneously. The present application also provides a nucleic acid molecule encoding the recombinant fusion protein, an expression vector containing the nucleic acid molecule, a method for producing the recombinant fusion protein and a method for treating a disease associated with over expression of CD47 and/or CD24 using the recombinant fusion protein.

18 Claims, 6 Drawing Sheets

Specification includes a Sequence Listing.

SEQUENCE LISTING

```
<160> NUMBER OF SEQ ID NOS: 36

<210> SEQ ID NO 1
<211> LENGTH: 125
<212> TYPE: PRT
<213> ORGANISM: Artificial Sequence
<220> FEATURE:
<223> OTHER INFORMATION: first extracellular Ig-like domain of SIRPalpha
      with mutation (SIRPalphaD1)

<400> SEQUENCE: 1

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro
        115                 120                 125

<210> SEQ ID NO 2
<211> LENGTH: 117
<212> TYPE: PRT
<213> ORGANISM: Artificial Sequence
<220> FEATURE:
<223> OTHER INFORMATION: IMM47 and IMM47C's heavy chain variable region

<400> SEQUENCE: 2

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95
```

```
Ala Arg Gly Ala Asp Tyr Ala Leu Asp Tyr Trp Gly Gln Arg Thr Ser
                100                 105                 110

Val Thr Val Ser Ser
            115

<210> SEQ ID NO 3
<211> LENGTH: 113
<212> TYPE: PRT
<213> ORGANISM: Artificial Sequence
<220> FEATURE:
<223> OTHER INFORMATION: IMM47's light chain variable region

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Asn Phe Ile Tyr Pro Leu Thr Phe Gly Gly Gly Thr Lys Val Glu Leu
            100                 105                 110

Lys

<210> SEQ ID NO 4
<211> LENGTH: 113
<212> TYPE: PRT
<213> ORGANISM: Artificial Sequence
<220> FEATURE:
<223> OTHER INFORMATION: IMM47C's light chain variable region

<400> SEQUENCE: 4

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly His
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Asn Phe Ile Tyr Pro Leu Thr Phe Gly Ala Gly Thr Lys Leu Glu Leu
            100                 105                 110

Lys

<210> SEQ ID NO 5
<211> LENGTH: 117
<212> TYPE: PRT
<213> ORGANISM: Artificial Sequence
<220> FEATURE:
<223> OTHER INFORMATION: IMM47H's heavy chain variable region
```

<400> SEQUENCE: 5

```
Asp Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ala Asp Tyr Ala Leu Asp Tyr Trp Gly Arg Thr Ser
            100                 105                 110

Val Thr Val Ser Ser
        115
```

<210> SEQ ID NO 6
<211> LENGTH: 113
<212> TYPE: PRT
<213> ORGANISM: Artificial Sequence
<220> FEATURE:
<223> OTHER INFORMATION: IMM47H's light chain variable region

<400> SEQUENCE: 6

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asn Phe Ile Tyr Pro Leu Thr Phe Gly Gly Gly Thr Lys Val Glu Leu
            100                 105                 110

Lys
```

<210> SEQ ID NO 7
<211> LENGTH: 9
<212> TYPE: PRT
<213> ORGANISM: Artificial Sequence
<220> FEATURE:
<223> OTHER INFORMATION: IMM47, IMM47C and IMM47H's heavy chain CDR1
      (HV-CDR-1)

<400> SEQUENCE: 7

```
Gly Tyr Ser Ile Thr Ser Gly Tyr Ser
1               5
```

<210> SEQ ID NO 8
<211> LENGTH: 7
<212> TYPE: PRT
<213> ORGANISM: Artificial Sequence

```
<220> FEATURE:
<223> OTHER INFORMATION: IMM47, IMM47C and IMM47H's heavy chain CDR2
      (HV-CDR-2)

<400> SEQUENCE: 8

Ile His Tyr Ser Gly Ser Thr
1               5

<210> SEQ ID NO 9
<211> LENGTH: 10
<212> TYPE: PRT
<213> ORGANISM: Artificial Sequence
<220> FEATURE:
<223> OTHER INFORMATION: IMM47, IMM47C and IMM47H's heavy chain CDR3
      (HV-CDR-3)

<400> SEQUENCE: 9

Ala Arg Gly Ala Asp Tyr Ala Leu Asp Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: IMM47, IMM47C and IMM47H's light chain CDR1
      (LV-CDR-1)

<400> SEQUENCE: 10

Gln Ser Leu Leu Tyr Ser Ser Asn Gln Lys Asn Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: IMM47, IMM47C and IMM47H's light chain CDR2
      (LV-CDR-2)

<400> SEQUENCE: 11

Trp Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: IMM47, IMM47C and IMM47H's light chain CDR3
      (LV-CDR-3)

<400> SEQUENCE: 12

Gln Gln Asn Phe Ile Tyr Pro Leu Thr
1               5

<210> SEQ ID NO 13
<211> LENGTH: 330
<212> TYPE: PRT
<213> ORGANISM: Artificial Sequence
<220> FEATURE:
<223> OTHER INFORMATION: IMM47, IMM47C and IMM47H's heavy chain constant
      region
```

<400> SEQUENCE: 13

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ala Ala Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 14
<211> LENGTH: 107
<212> TYPE: PRT
<213> ORGANISM: Artificial Sequence
<220> FEATURE:
<223> OTHER INFORMATION: IMM47, IMM47C and IMM47H's light chain constant region

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 15
<212> TYPE: PRT
<213> ORGANISM: Artificial Sequence
<220> FEATURE:
<223> OTHER INFORMATION: Linker

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Linker

<400> SEQUENCE: 16

Gly Gly Gly Gly Ser Gly Gly Gly Gly Ser
1               5                   10

<210> SEQ ID NO 17
<211> LENGTH: 20
<212> TYPE: PRT
<213> ORGANISM: Artificial Sequence
<220> FEATURE:
<223> OTHER INFORMATION: Linker

<400> SEQUENCE: 17

Gly Gly Gly Gly Ser Gly Gly Gly Gly Ser Gly Gly Gly Gly Ser Gly
1               5                   10                  15

Gly Gly Gly Ser
            20

<210> SEQ ID NO 18
<211> LENGTH: 587
<212> TYPE: PRT
<213> ORGANISM: Artificial Sequence
<220> FEATURE:
<223> OTHER INFORMATION: IMM4701C's long chain (SIRPalphaD1-linker-
    IMM47C's heavy chain)

```
<400> SEQUENCE: 18

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Gly Gly Gly
        115                 120                 125

Gly Ser Gly Gly Gly Ser Gly Gly Gly Ser Asp Val Gln Leu
130                 135                 140

Gln Glu Ser Gly Pro Asp Leu Val Lys Pro Ser Gln Ser Leu Ser Leu
145                 150                 155                 160

Thr Cys Thr Val Thr Gly Tyr Ser Ile Thr Ser Gly Tyr Ser Trp His
                165                 170                 175

Trp Ile Arg Gln Phe Pro Gly Asn Lys Leu Glu Trp Met Gly Tyr Ile
            180                 185                 190

His Tyr Ser Gly Ser Thr Lys Tyr Asn Pro Ser Leu Lys Ser Arg Ile
        195                 200                 205

Ser Ile Thr Arg Asp Thr Ser Lys Asn Gln Phe Phe Leu Gln Leu Asn
    210                 215                 220

Ser Val Thr Thr Glu Asp Thr Ala Thr Tyr Phe Cys Ala Arg Gly Ala
225                 230                 235                 240

Asp Tyr Ala Leu Asp Tyr Trp Gly Gln Arg Thr Ser Val Thr Val Ser
                245                 250                 255

Ser Ala Ser Thr Lys Gly Pro Ser Val Phe Pro Leu Ala Pro Ser Ser
            260                 265                 270

Lys Ser Thr Ser Gly Gly Thr Ala Ala Leu Gly Cys Leu Val Lys Asp
        275                 280                 285

Tyr Phe Pro Glu Pro Val Thr Val Ser Trp Asn Ser Gly Ala Leu Thr
    290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Gln
                325                 330                 335

Thr Tyr Ile Cys Asn Val Asn His Lys Pro Ser Asn Thr Lys Val Asp
            340                 345                 350

Lys Arg Val Glu Pro Lys Ser Cys Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415
```

Trp Tyr Val Asp Gly Val Glu Val His Asn Ala Lys Thr Lys Pro Arg
            420                 425                 430

Glu Glu Gln Tyr Asn Ala Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Ala Ala Thr Ile Ser Lys Ala Lys
465                 470                 475                 480

Gly Gln Pro Arg Glu Pro Gln Val Tyr Thr Leu Pro Pro Ser Arg Glu
                485                 490                 495

Glu Met Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
    530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 19
<211> LENGTH: 1821
<212> TYPE: DNA
<213> ORGANISM: Artificial Sequence
<220> FEATURE:
<223> OTHER INFORMATION: IMM4701C's long chain (SIRPalphaD1-linker-
      IMM47C's heavy chain)

<400> SEQUENCE: 19
atgggatggt catgtatcat ccttttttctg gtagcaactg caactggagt acattcagag     60
gaggagctgc aggtgattca gcctgacaag tccgtatcag ttgcagctgg agagtcggcc    120
attctgcact gcactgtgac ctccctgatc cctgtggggc ccatccagtg gttcagagga    180
gctggaccag cccgggaatt aatctacaat caaaaagaag ccacttcccc cgggtaaca    240 actgtttcag agtccacaaa gagagaaaac atggactttt ccatcagcat cagtgccatc    300
accccagcag atgccggcac ctactactgt gtgaagttcc ggaaagggag ccctgacacg    360
gagtttaagt ctggagcagg cactgagctg tctgtgcgtg ccaaaccctc tgcccccgtg    420
gtatcgggcc ctggcggcgg tgggagcggc ggcggtggga gcggcggcgg gggctcggat    480
gtgcagcttc aggagtcagg acctgacctg gtgaaacctt ctcagtcact ttcactcacc    540
tgcactgtca ctggctactc catcaccagt ggttatagct ggcactggat ccggcagttt    600
ccaggaaaca aactggaatg gatgggctac atacactata gtggtagcac taagtacaac    660
ccatctctca aaagtcgaat ctctatcact cgagacacat ccaagaacca gttcttcctg    720
cagttgaatt ctgtgactac tgaggacaca gccacatatt tctgtgcaag aggcgcggac    780
tatgctttgg actactgggg tcaacgaacc tcagtcaccg tctcctcagc tagcaccaag    840
ggcccatcgg tcttccccct ggcaccctcc tccaagagca cctctggggg cacagcggcc    900
ctgggctgcc tggtcaagga ctacttcccc gaaccggtga cggtgtcgtg gaactcaggc    960
gccctgacca gcggcgtgca caccttcccg gctgtcctac agtcctcagg actctactcc   1020
ctcagcagcg tggtgaccgt gccctccagc agcttgggca cccagaccta catctgcaac   1080

-continued

```
gtgaatcaca agcccagcaa caccaaggtg acaagagag ttgagcccaa atcttgtgac      1140
aaaactcaca catgcccacc gtgcccagca cctgaactcc tggggggacc gtcagtcttc      1200
ctcttccccc caaaacccaa ggacaccctc atgatctccc ggaccctga ggtcacatgc       1260 gtggtggtgg acgtgagcca cgaagaccct gaggtcaagt tcaactggta tgtggacggc      1320
gtggaggtgc ataatgccaa gacaaagccg cgggaggagc agtacaacgc cacgtaccgt      1380
gtggtcagcg tcctcaccgt cctgcaccaa gactggctga atggcaagga gtacaagtgc      1440
aaggtctcca acaaagccct cccagccccc atcgccgcaa ccatctccaa agccaaaggg      1500
cagccccgag aaccacaggt gtacaccctg cccccatccc gggaggagat gaccaagaac      1560
caagtcagcc tgacctgcct ggtcaaaggc ttctatccca gcgacatcgc cgtggagtgg      1620
gagagcaatg ggcagccgga gaacaactac aagaccacgc ctcccgtgct ggactccgac      1680
ggctccttct tcctctattc caagctcacc gtggacaaga gcaggtggca gcaggggaac      1740
gtcttctcat gctccgtgat gcatgaggct ctgcacaacc actacacgca gaagagcctc      1800
tccctgtctc cgggcaaatg a                                                1821

<210> SEQ ID NO 20
<211> LENGTH: 220
<212> TYPE: PRT
<213> ORGANISM: Artificial Sequence
<220> FEATURE:
<223> OTHER INFORMATION: IMM4701C's short chain (IMM47C's light chain)

<400> SEQUENCE: 20

Asp Ile Val Met Ser Gln Ser Pro Ser Leu Ala Val Ser Val Gly
1               5                  10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly His
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Asn Phe Ile Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 21
<211> LENGTH: 862
<212> TYPE: DNA
<213> ORGANISM: Artificial Sequence
<220> FEATURE:
<223> OTHER INFORMATION: IMM4701C's short chain (IMM47C's light chain)

<400> SEQUENCE: 21
atggattcac aggcccaggt tcttatgtta ctgctgctat gggtatctgg tacctgtggg      60
gacattgtga tgtcacagtc tccatcctcc ctagctgtgt cagttggaga gaaggttact    120
atgagctgca agtccagtca gagcctttta tatagtagca atcaaaagaa ctacttggcc    180
tggtaccagc agaaaccagg gcactctcct aaactgctga tttactgggc atccactagg    240
gaatctgggg tccctgatcg cttcacaggc agtggatctg ggacagattt cactctcacc    300
atcagcagtg tgaaggctga agacctggca gtttattact gtcagcaaaa ttttatctat    360
ccgctcacgt tcggtgctgg gaccaagctg gagctgaaac gtgagttcta gaggatccat    420
ctgggataag catgctgttt ctgtctgtcc ctaacatgc cctgtgatta ccgcaaaca    480 acacacccaa gggcagaact tgttacttta aacaccatcc tgtttgcttc tttcctcagg    540
aactgtggct gcaccatctg tcttcatctt cccgccatct gatgagcagt tgaaatctgg    600
aactgcctct gttgtgtgcc tgctgaataa cttctatccc agagaggcca agtacagtg    660 gaaggtggat aacgccctcc aatcgggtaa ctcccaggag agtgtcacag agcaggacag    720
caaggacagc acctacagcc tcagcagcac cctgacgctg agcaaagcag actacgagaa    780
acacaaagtc tacgcctgcg aagtcaccca tcagggcctg agctcgcccg tcacaaagag    840
cttcaacagg ggagagtgtt ag                                             862

<210> SEQ ID NO 22
<211> LENGTH: 220
<212> TYPE: PRT
<213> ORGANISM: Artificial Sequence
<220> FEATURE:
<223> OTHER INFORMATION: IMM4701's short chain (IMM47's light chain)

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Asn Phe Ile Tyr Pro Leu Thr Phe Gly Gly Gly Thr Lys Val Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 23
<211> LENGTH: 859
<212> TYPE: DNA
<213> ORGANISM: Artificial Sequence
<220> FEATURE:
<223> OTHER INFORMATION: IMM4701's short chain (IMM47's light chain)

<400> SEQUENCE: 23

```
atgggatggt catgtatcat ccttttttctg gtagcaactg caactggagt acattcagac    60
attcagatga cacagagccc tagcagcctg agcgcctccg tgggcgacag agtgaccatc   120
acctgcaaga gcagccaaag cctgctgtac agcagcaatc agaagaacta cctggcctgg   180
tatcagcaga agcctggcaa ggcccctaag ctgctgatct actgggcctc acaagagag   240
agcggcgtgc ctagcagatt cagcggcagc ggcagcggca ccgacttcac cctgaccatc   300
agcagcctgc agcctgagga cttcgccacc tactactgtc agcagaactt catctaccct   360
ctgaccttcg gcggaggcac caaggtggag ctgaagcgtg agttctagag gatccatctg   420
ggataagcat gctgttttct gtctgtccct aacatgccct gtgattatcc gcaaacaaca   480
cacccaaggg cagaactttg ttacttaaac accatcctgt ttgcttcttt cctcaggaac   540
tgtggctgca ccatctgtct tcatcttccc gccatctgat gagcagttga atctggaac   600
tgcctctgtt gtgtgcctgc tgaataactt ctatcccaga gaggccaaag tacagtggaa   660
ggtggataac gccctccaat cgggtaactc ccaggagagt gtcacagagc aggacagcaa   720
ggacagcacc tacagcctca gcagcaccct gacgctgagc aaagcagact acgagaaaca   780
caaagtctac gcctgcgaag tcacccatca gggcctgagc tcgcccgtca caaagagctt   840
caacagggga gagtgttag                                                859
```

<210> SEQ ID NO 24
<211> LENGTH: 447
<212> TYPE: PRT
<213> ORGANISM: Artificial Sequence
<220> FEATURE:
<223> OTHER INFORMATION: IMM4702C's long chain (IMM47C's heavy chain)

<400> SEQUENCE: 24

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95
```

```
Ala Arg Gly Ala Asp Tyr Ala Leu Asp Tyr Trp Gly Gln Arg Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ala Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Ala Ala Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 25
<211> LENGTH: 1398
<212> TYPE: DNA
<213> ORGANISM: Artificial Sequence
<220> FEATURE:
<223> OTHER INFORMATION: IMM4702C's long chain (IMM47C's heavy chain)

<400> SEQUENCE: 25
atgagagtgc tgattctttt gtgcctgttc acagcctttc tggtatcct  gtctgatgtg      60 cagcttcagg agtcaggacc tgacctggtg aaaccttctc agtcactttc actcacctgc     120
```

-continued

```
actgtcactg gctactccat caccagtggt tatagctggc actggatccg gcagttccca      180
ggaaacaaac tggaatggat gggctacata cactatagtg gtagcactaa gtacaaccca      240
tctctcaaaa gtcgaatctc tatcactcga gacacatcca agaaccagtt cttcctgcag      300
ttgaattctg tgactactga ggacacagcc acatatttct gtgcaagagg cgcggactat      360
gctttggact actggggtca acgaacctca gtcaccgtct cctcagctag caccaagggc      420
ccatcggtct tccccctggc accctcctcc aagagcacct ctgggggcac agcggccctg      480
ggctgcctgg tcaaggacta cttccccgaa ccggtgacgg tgtcgtggaa ctcaggcgcc      540
ctgaccagcg gcgtgcacac cttcccggct gtcctacagt cctcaggact ctactccctc      600
agcagcgtgg tgaccgtgcc ctccagcagc ttgggcaccc agacctacat ctgcaacgtg      660
aatcacaagc ccagcaacac caaggtggac aagagagttg agcccaaatc ttgtgacaaa      720
actcacacat gcccaccgtg cccagcacct gaactcctgg ggggaccgtc agtcttcctc      780
ttccccccaa aacccaagga caccctcatg atctcccgga cccctgaggt cacatgcgtg      840
gtggtggacg tgagccacga agaccctgag gtcaagttca actggtatgt ggacggcgtg      900
gaggtgcata atgccaagac aaagccgcgg gaggagcagt acaacgccac gtaccgtgtg      960
gtcagcgtcc tcaccgtcct gcaccaagac tggctgaatg gcaaggagta caagtgcaag     1020
gtctccaaca aagccctccc agcccccatc gccgcaacca tctccaaagc caaagggcag     1080
ccccgagaac cacaggtgta cacctgcccc catcccggg aggagatgac caagaaccaa     1140
gtcagcctga cctgcctggt caaaggcttc tatcccagcg acatcgccgt ggagtgggag     1200
agcaatgggc agccggagaa caactacaag accacgcctc ccgtgctgga ctccgacggc     1260
tccttcttcc tctattccaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gcaaatga                                                    1398
```

<210> SEQ ID NO 26
<211> LENGTH: 360
<212> TYPE: PRT
<213> ORGANISM: Artificial Sequence
<220> FEATURE:
<223> OTHER INFORMATION: IMM4702C's short chain (SIRPalphaD1-linker-
    IMM47C's light chain)

<400> SEQUENCE: 26

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Gly Gly Gly
        115                 120                 125
```

Gly Ser Gly Gly Gly Ser Gly Gly Gly Ser Asp Ile Val Met
    130             135             140

Ser Gln Ser Pro Ser Ser Leu Ala Val Ser Val Gly Glu Lys Val Thr
145                 150                 155                 160

Met Ser Cys Lys Ser Ser Gln Ser Leu Leu Tyr Ser Ser Asn Gln Lys
                165                 170                 175

Asn Tyr Leu Ala Trp Tyr Gln Gln Lys Pro Gly His Ser Pro Lys Leu
            180                 185                 190

Leu Ile Tyr Trp Ala Ser Thr Arg Glu Ser Gly Val Pro Asp Arg Phe
        195                 200                 205

Thr Gly Ser Gly Ser Gly Thr Asp Phe Thr Leu Thr Ile Ser Ser Val
210                 215                 220

Lys Ala Glu Asp Leu Ala Val Tyr Tyr Cys Gln Gln Asn Phe Ile Tyr
225                 230                 235                 240

Pro Leu Thr Phe Gly Ala Gly Thr Lys Leu Glu Leu Lys Arg Thr Val
                245                 250                 255

Ala Ala Pro Ser Val Phe Ile Phe Pro Pro Ser Asp Glu Gln Leu Lys
            260                 265                 270

Ser Gly Thr Ala Ser Val Val Cys Leu Leu Asn Asn Phe Tyr Pro Arg
        275                 280                 285

Glu Ala Lys Val Gln Trp Lys Val Asp Asn Ala Leu Gln Ser Gly Asn
290                 295                 300

Ser Gln Glu Ser Val Thr Glu Gln Asp Ser Lys Asp Ser Thr Tyr Ser
305                 310                 315                 320

Leu Ser Ser Thr Leu Thr Leu Ser Lys Ala Asp Tyr Glu Lys His Lys
                325                 330                 335

Val Tyr Ala Cys Glu Val Thr His Gln Gly Leu Ser Ser Pro Val Thr
            340                 345                 350

Lys Ser Phe Asn Arg Gly Glu Cys
        355                 360

<210> SEQ ID NO 27
<211> LENGTH: 1279
<212> TYPE: DNA
<213> ORGANISM: Artificial Sequence
<220> FEATURE:
<223> OTHER INFORMATION: IMM4702C's short chain (SIRPalphaD1-linker-
      IMM47C's light chain)

<400> SEQUENCE: 27
atgggatggt catgtatcat ccttttttctg gtagcaactg caactggagt acattcagag      60
gaggagctgc aggtgattca gcctgacaag tccgtatcag ttgcagctgg agagtcggcc     120
attctgcact gcactgtgac ctccctgatc cctgtggggc ccatccagtg gttcagagga     180
gctggaccag cccgggaatt aatctacaat caaaaagaag ccacttcccc cgggtaaca     240 actgtttcag agtccacaaa gagagaaaac atggactttt ccatcagcat cagtgccatc     300
accccagcag atgccggcac ctactactgt gtgaagttcc ggaaagggag ccctgacacg     360
gagtttaagt ctggagcagg cactgagctg tctgtgcgtg ccaaaccctc tgccccgtg      420 gtatcgggcc ctggcggcgg tgggagcggc ggcggtggga gcggcggcgg gggctcggac     480
attgtgatgt cacagtctcc atcctcccta gctgtgtcag ttggagagaa ggttactatg     540
agctgcaagt ccagtcagag ccttttatat agtagcaatc aaaagaacta cttggcctgg     600
taccagcaga aaccagggca ctctcctaaa ctgctgattt actgggcatc cactaggaa      660 tctggggtcc ctgatcgctt cacaggcagt ggatctggga cagatttcac tctcaccatc     720

```
agcagtgtga aggctgaaga cctggcagtt tattactgtc agcaaaattt tatctatccg    780
ctcacgttcg gtgctgggac caagctggag ctgaagcgtg agttctagag gatccatctg    840
ggataagcat gctgttttct gtctgtccct aacatgccct gtgattatcc gcaaacaaca    900
cacccaaggg cagaactttg ttacttaaac accatcctgt ttgcttcttt cctcaggaac    960
tgtggctgca ccatctgtct tcatcttccc gccatctgat gagcagttga aatctggaac   1020
tgcctctgtt gtgtgcctgc tgaataactt ctatcccaga gaggccaaag tacagtggaa   1080
ggtggataac gccctccaat cgggtaactc ccaggagagt gtcacagagc aggacagcaa   1140
ggacagcacc tacagcctca gcagcaccct gacgctgagc aaagcagact acgagaaaca   1200
caaagtctac gcctgcgaag tcacccatca gggcctgagc tcgcccgtca caaagagctt   1260
caacagggga gagtgttag                                                1279
```

```
<210> SEQ ID NO 28
<211> LENGTH: 447
<212> TYPE: PRT
<213> ORGANISM: Artificial Sequence
<220> FEATURE:
<223> OTHER INFORMATION: IMM4702H's long chain (IMM47H's heavy chain)

<400> SEQUENCE: 28
```

```
Asp Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ala Asp Tyr Ala Leu Asp Tyr Trp Gly Gln Arg Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ala Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Ala Ala Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 29
<211> LENGTH: 1401
<212> TYPE: DNA
<213> ORGANISM: Artificial Sequence
<220> FEATURE:
<223> OTHER INFORMATION: IMM4702H's long chain (IMM47H's heavy chain)

<400> SEQUENCE: 29
atgggatggt catgtatcat cctttttctg gtagcaactg caactggagt acattcagac      60
gtgcagctgc aagagagcgg ccctggcctg gtgaagccta gcgagaccct gagcctgacc     120
tgcaccgtgt ccggctacag catcacaagc ggctacagct ggcactggat cagacagcct     180
cctggcaagg gcctggagtg gatcggctac atccactaca gcggcagcac caagtacaac     240
cctagcctga gagcagagt gaccatcagc gtggacacaa gcaagaatca gttcagcctg     300
aagctgagca gcgtgaccgc cgccgacacc gccgtgtact actgcgctag aggcgccgac     360
tacgccctgg actactgggg acagagaaca agcgtgaccg tgagcagcgc tagcaccaag     420
ggcccatcgg tcttccccct ggcaccctcc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gctgtcctac agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta tgtggacggc     900
gtggaggtgc ataatgccaa gacaaagccg cgggaggagc agtacaacgc cacgtaccgt     960
gtggtcagcg tcctcaccgt cctgcaccaa gactggctga atggcaagga gtacaagtgc    1020
```

-continued

```
aaggtctcca acaaagccct cccagccccc atcgccgcaa ccatctccaa agccaaaggg    1080 cagcccgag  aaccacaggt gtacaccctg cccccatccc gggaggagat gaccaagaac    1140
caagtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctattc caagctcacc gtggacaaga gcaggtggca gcaggggaac    1320
gtcttctcat gctccgtgat gcatgaggct ctgcacaacc actacacgca gaagagcctc    1380
tccctgtctc cgggcaaatg a                                              1401
```

<210> SEQ ID NO 30
<211> LENGTH: 360
<212> TYPE: PRT
<213> ORGANISM: Artificial Sequence
<220> FEATURE:
<223> OTHER INFORMATION: IMM4702H's short chain (SIRPalphaD1-linker-
      IMM47H's light chain)

<400> SEQUENCE: 30

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Gly Gly Gly
        115                 120                 125

Gly Ser Gly Gly Gly Gly Ser Gly Gly Gly Gly Ser Asp Ile Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Leu Leu Tyr Ser Ser Asn Gln Lys
                165                 170                 175

Asn Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Asn Phe Ile Tyr
225                 230                 235                 240

Pro Leu Thr Phe Gly Gly Gly Thr Lys Val Glu Leu Lys Arg Thr Val
                245                 250                 255

Ala Ala Pro Ser Val Phe Ile Phe Pro Pro Ser Asp Glu Gln Leu Lys
            260                 265                 270

Ser Gly Thr Ala Ser Val Val Cys Leu Leu Asn Asn Phe Tyr Pro Arg
        275                 280                 285
```

```
Glu Ala Lys Val Gln Trp Lys Val Asp Asn Ala Leu Gln Ser Gly Asn
290                 295                 300
Ser Gln Glu Ser Val Thr Glu Gln Asp Ser Lys Asp Ser Thr Tyr Ser
305                 310                 315                 320
Leu Ser Ser Thr Leu Thr Leu Ser Lys Ala Asp Tyr Glu Lys His Lys
                325                 330                 335
Val Tyr Ala Cys Glu Val Thr His Gln Gly Leu Ser Ser Pro Val Thr
            340                 345                 350
Lys Ser Phe Asn Arg Gly Glu Cys
        355                 360
```

<210> SEQ ID NO 31
<211> LENGTH: 1279
<212> TYPE: DNA
<213> ORGANISM: Artificial Sequence
<220> FEATURE:
<223> OTHER INFORMATION: IMM4702H's short chain (SIRPalphaD1-linker-
      IMM47H's light chain)

<400> SEQUENCE: 31

```
atgggatggt catgtatcat ccttttctg gtagcaactg caactggagt acattcagag      60
gaggagctgc aggtgattca gcctgacaag tccgtatcag ttgcagctgg agagtcggcc    120
attctgcact gcactgtgac ctccctgatc cctgtggggc ccatccagtg gttcagagga    180
gctggaccag cccgggaatt aatctacaat caaaagaag ccacttccc ccgggtaaca    240
actgtttcag agtccacaaa gagagaaaac atggactttt ccatcagcat cagtgccatc    300
accccagcag atgccggcac ctactactgt gtgaagttcc ggaaagggag ccctgacacg    360
gagtttaagt ctggagcagg cactgagctg tctgtgcgtg ccaaaccctc tgccccgtg     420
gtatcgggcc ctggcggcgg tgggagcggc ggcggtggga gcggcggcgg gggctcggac    480
atcgtgatga cacagagccc tgacagcctg gccgtgagcc tgggcgagag agccaccatc    540
aactgcaaga gctctcagag cctgctgtac agcagcaatc agaagaacta cctggcctgg    600
tatcagcaga gccctggaca gcctcctaag ctgctgatct actgggcaag cacaagagag    660
agcggcgtgc ctgacagatt cagcggcagc ggcagcggca ccgacttcac cctgaccatc    720
agcagcctgc aagccgagga cgtggccgtg tactactgtc agcagaactt catctaccct    780
ctgaccttcg gcggcggcac caaggtggag ctgaagcgtg agttctagag gatccatctg    840
ggataagcat gctgttttct gtctgtccct aacatgccct gtgattatcc gcaaacaaca    900
cacccaaggg cagaactttg ttacttaaac accatcctgt ttgcttcttt cctcaggaac    960
tgtggctgca ccatctgtct tcatcttccc gccatctgat gagcagttga atctggaac    1020
tgcctctgtt gtgtgcctgc tgaataactt ctatcccaga gaggccaaag tacagtggaa    1080
ggtggataac gccctccaat cgggtaactc ccaggagagt gtcacagagc aggacagcaa    1140
ggacagcacc tacagcctca gcagcaccct gacgctgagc aaagcagact acgagaaaca    1200
caaagtctac gcctgcgaag tcacccatca gggcctgagc tcgcccgtca caagagctt    1260
caacagggga gagtgttag                                                1279
```

<210> SEQ ID NO 32
<211> LENGTH: 364
<212> TYPE: PRT
<213> ORGANISM: Artificial Sequence
<220> FEATURE:
<223> OTHER INFORMATION: SIRPalphaD1 mutant-Fc (IMM01)

-continued

<400> SEQUENCE: 32

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Glu Pro Lys Ser Cys Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly
        355                 360

<210> SEQ ID NO 33
<211> LENGTH: 1095
<212> TYPE: DNA
<213> ORGANISM: Artificial Sequence
<220> FEATURE:
<223> OTHER INFORMATION: SIRPalphaD1 mutant-Fc (IMM01)

<400> SEQUENCE: 33

```
gaggaggagc tgcaggtgat tcagcctgac aagtccgtat cagttgcagc tggagagtcg    60
gccattctgc actgcactgt gacctccctg atccctgtgg ggcccatcca gtggttcaga   120
ggagctggac cagcccggga attaatctac aatcaaaaag aaggccactt ccccgggta    180
acaactgttt cagagtccac aaagagagaa acatggact tttccatcag catcagtgcc   240
atcaccccag cagatgccgg cacctactac tgtgtgaagt tccggaaagg gagccctgac   300
acggagttta gtctggagc aggcactgag ctgtctgtgc gtgccaaacc ctctgccccc    360
gtggtatcgg gccctgcggc gagggccaca cctcagcacg agcccaaatc ttgtgacaaa   420
actcacacat gcccaccgtg cccagcacct gaactcctgg ggaccgtc agtcttcctc     480
ttccccccaa aacccaagga caccctcatg atctcccgga cccctgaggt cacatgcgtg   540
gtggtggacg tgagccacga agaccctgag gtcaagttca actggtacgt ggacggcgtg   600
gaggtgcata atgccaagac aaagccgcgg gaggagcagt acaacagcac gtaccgtgtg   660
gtcagcgtcc tcaccgtcct gcaccaggac tggctgaatg caaggagta caagtgcaag   720
gtctccaaca aagccctccc agccccatc gagaaaacca tctccaaagc caagggcag    780
ccccgagaac cacaggtgta caccctgccc ccatcccggg atgagctgac caagaaccag   840
gtcagcctga cctgcctggt caaaggcttc tatcccagcg acatcgccgt ggagtgggag   900
agcaatgggc agccggagaa caactacaag accacgcctc ccgtgctgga ctccgacggc   960
tccttcttcc tctacagcaa gctcaccgtg gacaagagca ggtggcagca ggggaacgtc  1020
ttctcatgct ccgtgatgca tgaggctctg cacaaccact acacgcagaa gagcctctcc  1080
ctgtctccgg gttga                                                   1095
```

<210> SEQ ID NO 34
<211> LENGTH: 57
<212> TYPE: DNA
<213> ORGANISM: Artificial Sequence
<220> FEATURE:
<223> OTHER INFORMATION: nucleotide encoding mouse IgG1 heavy chain signal peptide

<400> SEQUENCE: 34

```
atgggatggt catgtatcat ccttttctg gtagcaactg caactggagt acattca       57
```

<210> SEQ ID NO 35
<211> LENGTH: 9
<212> TYPE: DNA
<213> ORGANISM: Artificial Sequence
<220> FEATURE:
<223> OTHER INFORMATION: Kozak consensus sequence

<400> SEQUENCE: 35

```
gccgccacc                                                             9
```

<210> SEQ ID NO 36
<211> LENGTH: 597
<212> TYPE: PRT
<213> ORGANISM: Artificial Sequence
<220> FEATURE:
<223> OTHER INFORMATION: human SIRPalpha-mouse IgG1 Fc

```
<400> SEQUENCE: 36

Met Gly Trp Ser Cys Ile Ile Leu Phe Leu Val Ala Thr Ala Thr Gly
1               5                   10                  15

Val His Ser Ser Cys Ala Trp Ser Gly Val Ala Gly Glu Glu Glu Leu
            20                  25                  30

Gln Val Ile Gln Pro Asp Lys Ser Val Ser Val Ala Ala Gly Glu Ser
        35                  40                  45

Ala Ile Leu His Cys Thr Val Thr Ser Leu Ile Pro Val Gly Pro Ile
    50                  55                  60

Gln Trp Phe Arg Gly Ala Gly Pro Ala Arg Glu Leu Ile Tyr Asn Gln
65                  70                  75                  80

Lys Glu Gly His Phe Pro Arg Val Thr Thr Val Ser Glu Ser Thr Lys
                85                  90                  95

Arg Glu Asn Met Asp Phe Ser Ile Ser Ile Ser Asn Ile Thr Pro Ala
            100                 105                 110

Asp Ala Gly Thr Tyr Tyr Cys Val Lys Phe Arg Lys Gly Ser Pro Asp
        115                 120                 125

Thr Glu Phe Lys Ser Gly Ala Gly Thr Glu Leu Ser Val Arg Ala Lys
    130                 135                 140

Pro Ser Ala Pro Val Val Ser Gly Pro Ala Ala Arg Ala Thr Pro Gln
145                 150                 155                 160

His Thr Val Ser Phe Thr Cys Glu Ser His Gly Phe Ser Pro Arg Asp
                165                 170                 175

Ile Thr Leu Lys Trp Phe Lys Asn Gly Asn Glu Leu Ser Asp Phe Gln
            180                 185                 190

Thr Asn Val Asp Pro Val Gly Glu Ser Val Ser Tyr Ser Ile His Ser
        195                 200                 205

Thr Ala Lys Val Val Leu Thr Arg Glu Asp Val His Ser Gln Val Ile
    210                 215                 220

Cys Glu Val Ala His Val Thr Leu Gln Gly Asp Pro Leu Arg Gly Thr
225                 230                 235                 240

Ala Asn Leu Ser Glu Thr Ile Arg Val Pro Pro Thr Leu Glu Val Thr
                245                 250                 255

Gln Gln Pro Val Arg Ala Glu Asn Gln Val Asn Val Thr Cys Gln Val
            260                 265                 270

Arg Lys Phe Tyr Pro Gln Arg Leu Gln Leu Thr Trp Leu Glu Asn Gly
        275                 280                 285

Asn Val Ser Arg Thr Glu Thr Ala Ser Thr Val Thr Glu Asn Lys Asp
    290                 295                 300

Gly Thr Tyr Asn Trp Met Ser Trp Leu Leu Val Asn Val Ser Ala His
305                 310                 315                 320

Arg Asp Asp Val Lys Leu Thr Cys Gln Val Glu His Asp Gly Gln Pro
                325                 330                 335

Ala Val Ser Lys Ser His Asp Leu Lys Val Ser Ala His Pro Lys Glu
            340                 345                 350

Gln Gly Ser Asn Thr Ala Ala Glu Asn Thr Gly Ser Asn Glu Arg Asn
        355                 360                 365

Glu Phe Val Pro Arg Asp Cys Gly Cys Lys Pro Cys Ile Cys Thr Val
    370                 375                 380

Pro Glu Val Ser Ser Val Phe Ile Phe Pro Pro Lys Pro Lys Asp Val
385                 390                 395                 400

Leu Thr Ile Thr Leu Thr Pro Lys Val Thr Cys Val Val Val Asp Ile
                405                 410                 415
```

```
Ser Lys Asp Asp Pro Glu Val Gln Phe Ser Trp Phe Val Asp Asp Val
            420                 425                 430

Glu Val His Thr Ala Gln Thr Gln Pro Arg Glu Glu Gln Phe Asn Ser
        435                 440                 445

Thr Phe Arg Ser Val Ser Glu Leu Pro Ile Met His Gln Asp Trp Leu
    450                 455                 460

Asn Gly Lys Glu Phe Lys Cys Arg Val Asn Ser Ala Ala Phe Pro Ala
465                 470                 475                 480

Pro Ile Glu Lys Thr Ile Ser Lys Thr Lys Gly Arg Pro Lys Ala Pro
                485                 490                 495

Gln Val Tyr Thr Ile Pro Pro Pro Lys Glu Gln Met Ala Lys Asp Lys
            500                 505                 510

Val Ser Leu Thr Cys Met Ile Thr Asp Phe Phe Pro Glu Asp Ile Thr
        515                 520                 525

Val Glu Trp Gln Trp Asn Gly Gln Pro Ala Glu Asn Tyr Lys Asn Thr
    530                 535                 540

Gln Pro Ile Met Asn Thr Asn Gly Ser Tyr Phe Val Tyr Ser Lys Leu
545                 550                 555                 560

Asn Val Gln Lys Ser Asn Trp Glu Ala Gly Asn Thr Phe Thr Cys Ser
                565                 570                 575

Val Leu His Glu Gly Leu His Asn His His Thr Glu Lys Ser Leu Ser
            580                 585                 590

His Ser Pro Gly Lys
            595
```

RECOMBINANT FUSION PROTEINS TARGETING CD47 AND CD24, PREPARATION AND USE THEREOF

RELATED APPLICATIONS AND INCORPORATION BY REFERENCE

This application claims priority to Chinese Patent Application No. 202111195248.4 filed on Oct. 13, 2021.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a replacement Sequence Listing which was created on Nov. 28, 2021 and amended on Dec. 9, 2021 and has been submitted electronically and is hereby incorporated by reference in its entirety. Said ASCII copy, is named Replacement55525_00050_ST_EN.txt and is 60.121 bytes in size.

FIELD OF THE INVENTION

The application relates to a recombinant fusion protein targeting CD47, CD24 and/or FcR, and its preparation and use thereof, especially its use in tumor therapies.

BACKGROUND OF THE INVENTION

Cancer cells have developed several mechanisms to evade hosts' immune surveillance, including: 1) to highly express membrane CD24 proteins that bind Siglec-10 receptors on immune cells to inhibit immune activation, so as to evade immune surveillance by macrophages, T-lymphocytes, B-lymphocytes and natural killer (NK) cells; 2) to express a high level of CD47s, which bind to the signal regulatory protein alpha (SIRPα) on macrophage surfaces, inducing inhibitory signals that inhibit phagocytosis of cancer cells by macrophages. It can be seen that the cancer cells are quite "smart" and reproduce quickly depending on their developed evasion mechanisms. Accordingly, development of effective anti-cancer drugs for killing the cancer cells may focus on targeting these mechanisms.

SIRP and CD47

Signal regulatory protein (SIRP) is a trans-membrane glycoprotein, having three family members, SIRPα (CD172a), SIRPβ (CD172b) and SIRPγ (CD172g). The three proteins comprise similar extracellular regions but distinct intracellular domains. The extracellular region contains three immunoglobulin-like domains, one IgV-set and two IgC-set domains. The intracellular domain of SIRPα (CD172a) contains two inhibitory signaling regions that can inhibit signal transduction and corresponding cell functions. SIRPβ (CD172b) and SIRPγ (CD172g) have very short intracellular regions without any signal transduction domain. However, SIRPβ (CD172b) may function through an adaptor protein, e.g., DAP12 for signal transduction. SIRPs are mainly expressed on macrophages (Mφ), dendritic cells (DCs) and neurons.

CD47 is a transmembrane glycoprotein belonging to the immunoglobulin superfamily, and is expressed on the surface of all cell types including red blood cells. Ligands for CD47 include integrins, thrombospondin-1 and SIRPs. CD47, by interacting with SIRPα to emit a 'don't eat me' signal, can inhibit phagocytosis by macrophages and thus protects cells, such as blood cells, from being attacked by macrophages.

Studies have shown that many tumor or cancer cells over-express CD47s, which prevent their phagocytosis by macrophages. Such cancer cells include cells of acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer. It is reported that injection of CD47 specific antibody that blocks the binding of CD47 to SIRPα can significantly inhibit tumor growth in tumor-bearing mice. Tumor or cancer cells were eliminated completely when the same antibody was injected into the mice carrying human leukemia cells (Theocharides A P A, et al., 2012).

CD24 and Siglec-10

The sialic acid-binding immunoglobulin (Ig)-like lectins (Siglecs) are immunoglobulin-like type I transmembrane proteins. Siglec-10, a Siglecs family member and an inhibitory receptor, is widely expressed on immune cells such as macrophages, B cells, NK cells and activated T cells. It has five extracellular Ig-like domains, a transmembrane region, and a cytoplasmic tail. The IgV structural domain of Siglec-10 contains a key arginine residue, which is related to the recognition of sialic acid (Yin, et al., 2020). Siglec-10 expression on T cells is known to interfere with T cell activation by inhibiting the formation of T cell major histocompatibility complex class I (MHC-I) peptide complex and phosphorylation of T cell receptor-associated kinase, Lck, and ZAP-70 (Yin, et al., 2020). Siglec-10 expression on B cells and NK cells inhibits BCR-mediated and NK cell receptor-mediated signal transduction, respectively (Yin, et al., 2020).

CD24 is a glycosyl-phosphatidylinositol-anchored protein found on surface of developing T and most B lymphocytes (Yin et al., 2020). It is highly expressed in various cancer cells including ovarian cancer, breast cancer, cervical cancer, endometrial cancer, acute lymphoblastic leukemia (ALL), cholangiocarcinoma, bladder cancer, pancreatic cancer, stomach adenocarcinoma, and glioblastoma (Barkal et al., 2019; Liu et al., 2013). CD24 on tumor cells interacts with Siglec-10 on immune cells to produce a 'don't eat me' signal for immune evasion and shielding tumor cells from immune attack.

CD24 expression is significantly associated with bladder tumor recurrence (Liu et al., 2013). In patients with ovarian cancer, expression of CD24 was also found to be an independent predictor of overall survival and correlate with tumor staging and peritoneal and lymph node metastasis; CD24-positive cells have enhanced proliferation, a highly invasive phenotype, and are associated with cisplatin resistance in ovarian cancer cells (Nakamura et al. 2017).

Anti-CD24 monoclonal antibodies are reported to reduce lung metastasis and prolong the overall survival in bladder cancer and triple-negative breast cancer mouse models. Literature also revealed that antibody blockade of CD24-Siglec-10 interaction resulted in a macrophage-dependent reduction of tumor growth and extension of survival in tumor-bearing mice (Barkal, et al., 2019; Chan et al., 2019; Overdevest et al., 2011).

In addition, previous studies demonstrated that anti-CD47/CD24 dual antibody treatment could effectively activate the myeloid immunity in the brain (Wu H, et al, 2021). And such dual treatment was revealed to augment phagocytosis against human ovarian cancer cells (Barkal et al., 2019). Barakal et al also found that compared to the either treatment alone, combination treatment of CD24 antibody and cetuximab further enhanced phagocytosis of pancreatic adenocarcinoma cells. All these indicate that combination therapies involving CD24 neutralization may produce synergistic anti-tumor effects.

Fc and FcR

The fragment crystallizable region (Fc region) is the tail region of an antibody and is the domain that determines the effector function of the antibody, that is, how it engages with specific cell receptors or other defense proteins.

An Fc receptor (FcR) is a protein found on the surface of certain cells, including B lymphocytes, follicular dendritic cells, natural killer cells, macrophages, neutrophils, eosinophils, basophils, and mast cells. These cells contribute to the protective functions of the immune system.

An Fc region may interact with Fc receptors and some proteins of the complement system, activating the immune system.

Therapeutic Bi-Specific or Multi-Specific Fusion Proteins Antibodies

Antibodies targeting a single tumor-associated antigen have been found to have limited therapeutic efficacy. For example, the overall response rate of an approved anti-PD-L1 antibody, Avelumab (BAVENCIO), is only 33%. Bi- or tri-specific fusion proteins have been developed in recent years, showing promising effects in pre-clinical and clinical tests.

Although attaching additional binding moieties to conventional antibodies seems conceptually straightforward, such modification significantly alters antibody structures and may compromise one another's affinity and/or efficacy (Wang S et al., 2021). In order to optimize in vivo efficacy and pharmaceutical properties, elaborate design and engineering should be given to choice of main and appended binding moieties (sequences), balanced affinities for targets, sites of attachment (N- or C-termini, heavy or light chains), structural stability, linker lengths and/or sequences (Shim H. 2020).

U.S. Pat. No. 10,800,821 B2 discloses a recombinant bi-functional fusion protein of about 90 kDa, targeting both CD47 and FcR, which was used to treat Balb/c nude mice carrying HL cells, and an enhanced anti-tumor effect was observed.

Citation or identification of any document in this application is not an admission that such document is available as prior art to the present disclosure.

SUMMARY OF THE INVENTION

The present application discloses a recombinant fusion protein, comprising an anti-CD24 antibody or an antibody fragment thereof, and a peptide specifically binding to CD47. Such a recombinant fusion protein shows better in vivo anti-tumor effect than the combination of the CD47 binding peptide and the anti-CD24 antibody.

Specifically, the present application discloses a recombinant fusion protein, comprising an anti-CD24 antibody or an antibody fragment thereof specifically binding CD24, and a CD47 binding peptide specifically binding to CD47, wherein the CD47 binding peptide is linked to the anti-CD24 antibody or antibody fragment thereof. The anti-CD24 antibody or antibody fragment thereof comprises a heavy chain variable region, a heavy chain constant region, and a light chain variable region, wherein the heavy chain variable region comprises a heavy chain variable CDR1 (HV-CDR1), a heavy chain variable CDR2 (HV-CDR2) and a heavy chain variable CDR3 (HV-CDR3) having amino acid sequences set forth in SEQ ID NOs: 7, 8 and 9, respectively, the light chain variable region comprises a light chain variable CDR1 (LV-CDR1), a light chain variable CDR2 (LV-CDR2) and a light chain variable CDR3 (LV-CDR3) having amino acid sequences set forth in SEQ ID NOs: 10, 11 and 12, respectively, and the heavy chain constant region has Fc binding affinity and is linked to C-terminus of the heavy chain variable region. The CD47 binding peptide comprises a mutated signal-regulatory protein (SIRP) extracellular domain, having an amino acid sequence having at least 95% sequence identity to SEQ ID NO: 1. The CD47 binding peptide may be linked to the N-terminus of the heavy chain variable region or the light chain variable region of the anti-CD24 antibody or antibody fragment thereof. The recombinant fusion protein of the disclosure can bind CD47, CD24 and FcR simultaneously.

The heavy chain variable region of the anti-CD24 antibody or antibody fragment thereof of the disclosure may comprise an amino acid sequence having at least 80%, 85%, 90%, 91%, 92%, 93%, 94%, 95%, 96%, 97%, 98% or 99% identity to SEQ ID NOs: 2 or 5. In certain embodiments, the heavy chain variable region may comprise the amino acid sequence of SEQ ID NOs: 2 or 5. The light chain variable region of the anti-CD24 antibody or antibody fragment thereof may comprise an amino acid sequence having at least 80%, 85%, 90%, 91%, 92%, 93%, 94%, 95%, 96%, 97%, 98% or 99% identity to SEQ ID NOs: 3, 4 or 6. In certain embodiments, the light chain variable region may comprise the amino acid sequence of SEQ ID NOs: 3, 4 or 6. In certain embodiments, the heavy chain variable region and the light chain variable region of the anti-CD24 antibody or antibody fragment thereof may comprise amino acid sequences having at least 80%, 85%, 90%, 91%, 92%, 93%, 94%, 95%, 96%, 97%, 98% or 99% identity to i) SEQ ID NOs: 2 and 3, respectively, ii) SEQ ID NOs: 2 and 4, respectively, or iii) SEQ ID NOs: 5 and 6, respectively. In certain embodiments, the heavy chain variable region and the light chain variable region of the anti-CD24 antibody or antibody fragment thereof may comprise amino acid sequences set forth in i) SEQ ID NOs: 2 and 3, respectively, ii) SEQ ID NOs: 2 and 4, respectively, or iii) SEQ ID NOs: 5 and 6, respectively.

The heavy chain constant region having FcR binding affinity may be naturally occurring or artificially engineered human IgG1, IgG2, IgG3 or IgG4 heavy chain constant region, or a functional fragment thereof. In certain embodiments, the heavy chain constant region having FcR binding affinity is human IgG1 heavy chain constant region, or a functional fragment thereof. In certain embodiments, the heavy chain constant region having FcR binding affinity comprises the amino acid sequence of SEQ ID NO: 13.

The anti-CD24 antibody or antibody fragment thereof may comprise a light chain constant region, such as human kappa light chain constant region, or a functional fragment thereof, linked to the C-terminus of the light chain variable region. In certain embodiments, the anti-CD24 antibody or antibody fragment thereof may comprise the amino acid sequence of SEQ ID NO: 14.

In certain embodiments, at least one paratope of the anti-CD24 antibody or antibody fragment thereof is linked to the CD47 binding peptide at N-terminus of the heavy chain variable region or the light chain variable region constituting the paratope. In certain embodiments, each paratope of the anti-CD24 antibody or antibody fragment thereof is linked to the CD47 binding peptide at N-terminus of the heavy chain variable region or the light chain variable region constituting the paratope. In certain embodiments, each paratope of the anti-CD24 antibody or antibody fragment thereof is linked to the CD47 binding peptide at N-terminus of the heavy chain variable region constituting the paratope. In certain embodiments, each paratope of the anti-CD24 antibody or antibody fragment thereof is linked to the CD47 binding peptide at N-terminus of the light chain variable region constituting the paratope.

The anti-CD24 antibody or antibody fragment thereof may be linked to the CD47 binding peptide via a linker. The linker may be a peptide linker made up of 5 to 30, 10 to 30, 10 to 20, or 15 amino acids. The linker may be e.g., -(Gly-Gly-Gly-Gly-Ser)$_2$-(SEQ ID NO: 16), -(Gly-Gly-Gly-Gly-Ser)$_3$-(SEQ ID NO: 15), or -(Gly-Gly-Gly-Gly-Ser)$_4$-(SEQ ID NO: 17). In certain embodiments, the linker is -(Gly-Gly-Gly-Gly-Ser)$_3$-(SEQ ID NO: 15).

The recombinant fusion protein of the disclosure may comprise a CD47 binding peptide-linker-anti-CD24 heavy chain fragment and an anti-CD24 light chain, wherein the CD47 binding peptide-linker-anti-CD24 heavy chain fragment may comprise an amino acid sequence having at least 80%, 85%, 90%, 91%, 92%, 93%, 94%, 95%, 96%, 97%, 98% or 99% identity to SEQ ID NO: 18, the anti-CD24 light chain may comprise an amino acid sequence having at least 80%, 85%, 90%, 91%, 92%, 93%, 94%, 95%, 96%, 97%, 98% or 99% identity to SEQ ID NOs: 20 or 22. In certain embodiments, the recombinant fusion protein of the disclosure may comprise a CD47 binding peptide-linker-anti-CD24 heavy chain fragment and an anti-CD24 light chain, wherein the CD47 binding peptide-linker-anti-CD24 heavy chain fragment may comprise the amino acid sequence of SEQ ID NO: 18, and the anti-CD24 light chain may comprise the amino acid sequence of SEQ ID NOs: 20 or 22. The amino acid sequences of SEQ ID NOs: 18, 20 and 22 may be encoded by nucleotide sequences of SEQ ID NOs: 19, 21 and 23, respectively.

The recombinant fusion protein of the disclosure may comprise an anti-CD24 heavy chain, and a CD47 binding peptide-linker-anti-CD24 light chain fragment, wherein the anti-CD24 heavy chain may comprise an amino acid sequence having at least 80%, 85%, 90%, 91%, 92%, 93%, 94%, 95%, 96%, 97%, 98% or 99% identity to SEQ ID NO: 24, and the CD47 binding peptide-linker-anti-CD24 light chain fragment may comprise an amino acid sequence having at least 80%, 85%, 90%, 91%, 92%, 93%, 94%, 95%, 96%, 97%, 98% or 99% identity to SEQ ID NO: 26. In certain embodiments, the recombinant fusion protein of the disclosure may comprise an anti-CD24 heavy chain, and a CD47 binding peptide-linker-anti-CD24 light chain fragment, wherein the anti-CD24 heavy chain may comprise the amino acid sequence of SEQ ID NO: 24, and the CD47 binding peptide-linker-anti-CD24 light chain fragment may comprise the amino acid sequence of SEQ ID NO: 26. The recombinant fusion protein of the disclosure may comprise an anti-CD24 heavy chain, and a CD47 binding peptide-linker-anti-CD24 light chain fragment, wherein the anti-CD24 heavy chain may comprise an amino acid sequence having at least 80%, 85%, 90%, 91%, 92%, 93%, 94%, 95%, 96%, 97%, 98% or 99% identity to SEQ ID NO: 28, and the CD47 binding peptide-linker-anti-CD24 light chain fragment may comprise an amino acid sequence having at least 80%, 85%, 90%, 91%, 92%, 93%, 94%, 95%, 96%, 97%, 98% or 99% identity to SEQ ID NO: 30. In certain embodiments, the recombinant fusion protein of the disclosure may comprise an anti-CD24 heavy chain, and a CD47 binding peptide-linker-anti-CD24 light chain fragment, wherein the anti-CD24 heavy chain may comprise the amino acid sequence of SEQ ID NO: 28, and the CD47 binding peptide-linker-anti-CD24 light chain fragment may comprise the amino acid sequence of SEQ ID NO: 30. The amino acid sequences of SEQ ID NOs: 24, 26, 28 and 30 may be encoded by the nucleotide sequences of SEQ ID NOs: 25, 27, 29 and 31, respectively.

The present application also provides a nucleic acid molecule encoding the recombinant fusion protein of the disclosure, as well as an expression vector comprising such a nucleic acid molecule and a host cell comprising such an expression vector. A method for preparing the recombinant fusion protein using the host cell of the disclosure is provided, comprising steps of (i) expressing the recombinant fusion protein in the host cell, and (ii) isolating the recombinant fusion protein from the host cell or its cell culture.

The application further provides a pharmaceutical composition which may comprise the recombinant fusion protein, the nucleic acid molecule, the expression vector, or the host cell, of the disclosure, and at least one pharmaceutically acceptable excipient. In certain embodiments, the pharmaceutical composition comprises at least one pharmaceutically acceptable adjuvant.

The recombinant fusion protein or pharmaceutical composition of the disclosure may be used in treatment of, or in preparation of a medicament for treating a disease associated with over-expression of CD47 and/or CD24.

In one aspect, the present application provides a method for treating or alleviating a disease associated with over-expression of CD47 and/or CD24 in a subject in need thereof, comprising administering to the subject a therapeutically effective amount of the pharmaceutical composition of the disclosure.

The disease associated with over-expression of CD47 and/or CD24 may be acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, renal cell carcinoma, cervical cancer, endometrial cancer, cholangiocarcinoma, stomach adenocarcinoma, and glioblastoma.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the application not to encompass within the application any previously known product, process of making the product, or method of using the product such that Applicants reserve the right and hereby disclose a disclaimer of any previously known product, process, or method. It is further noted that the application does not intend to encompass within the scope of the application any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the application to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the application.

DESCRIPTION OF THE DRAWINGS

The following detailed description, given by way of example, but not intended to limit the application solely to the specific embodiments described, may best be understood in conjunction with the accompanying drawings.

DETAILED DESCRIPTION OF THE APPLICATION

Figure 1:
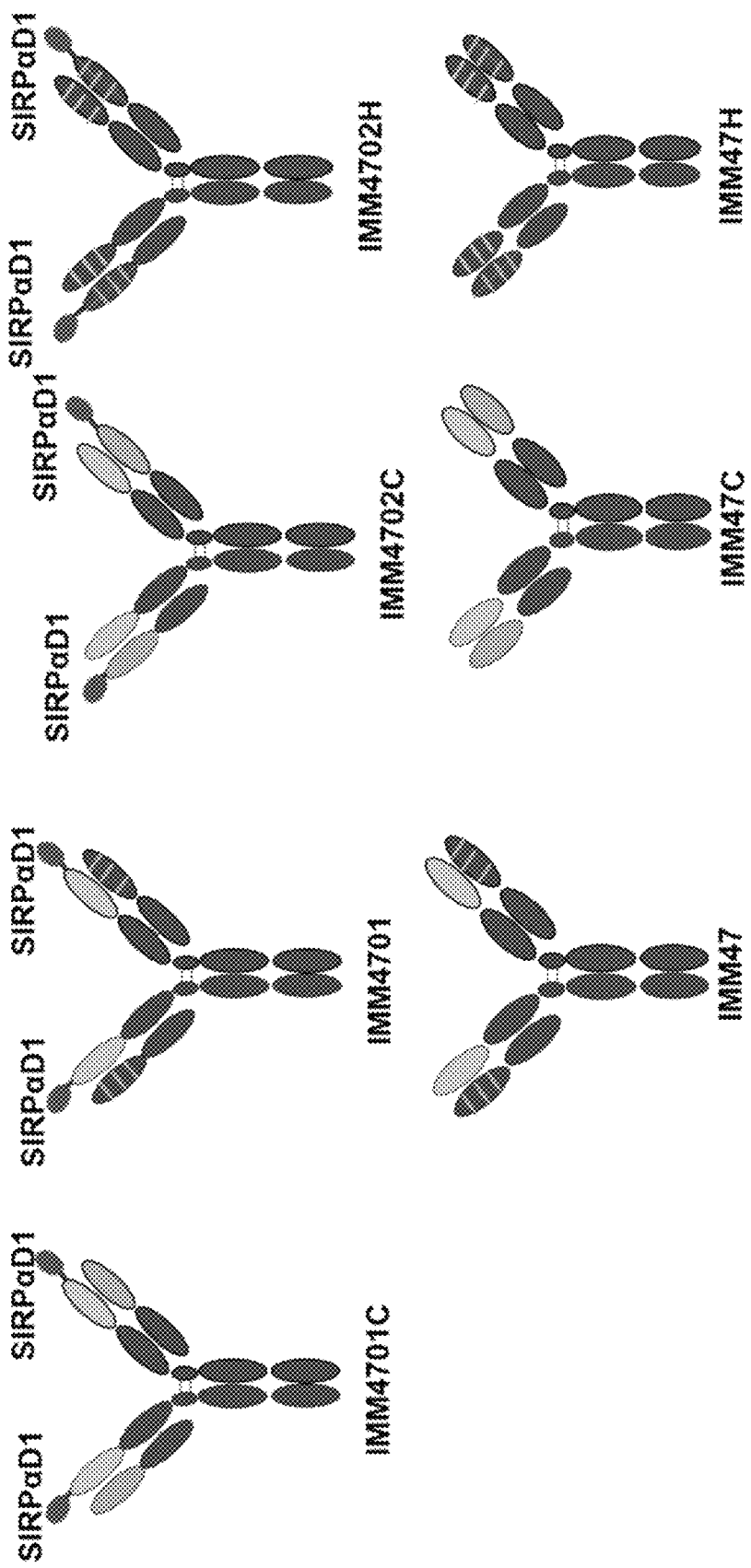
FIG. 1 is the schematic diagram of structures of the recombinant fusion proteins, IMM4701C, IMM4701, IMM4702C, and IMM4702H, of the present application. The circular "SIRPαD1" domain represents mutated extracellular domain 1 of SIRP alpha protein (SIRPαD1), which has the amino acid sequence set forth in SEQ ID NO: 1. In IMM4701C, the mutated SIRPαD1 is linked, via a linker peptide, to the N-terminus of the heavy chains of an anti-CD24 antibody IMM47C, wherein IMM47C is an IgG antibody having a mouse heavy chain variable region and a mouse light chain variable region. The linker has the amino acid sequence of SEQ ID NO: 15. IMM47C comprises a heavy chain variable region of SEQ ID NO: 2, a heavy chain constant region of SEQ ID NO: 13, a light chain variable region of SEQ ID NO: 4, and a light chain constant region of SEQ ID NO: 14. In IMM4701, the mutated SIRPαD1 is linked, via a linker peptide, to the N-terminus of the heavy chains of an anti-CD24 antibody IMM47, wherein IMM47 is an IgG antibody having a mouse heavy chain variable region and a humanized light chain variable region. IMM47 comprises a heavy chain variable region of SEQ ID NO: 2, a heavy chain constant region of SEQ ID NO: 13, a light chain variable region of SEQ ID NO: 3, and a light chain constant region of SEQ ID NO: 14. In IMM4702C, the mutated SIRPαD1 is linked, via a linker peptide, to the N-terminus of the light chains of IMM47C. In IMM4702H, the mutated SIRPαD1 is linked, via a linker peptide, to the N-terminus of the light chains of IMM47H, wherein IMM47H is an IgG antibody having a humanized heavy chain variable region and a humanized light chain variable region. IMM47H comprises a heavy chain variable region of SEQ ID NO: 5, a heavy chain constant region of SEQ ID NO: 13, a light chain variable region of SEQ ID NO: 6, and a light chain constant region of SEQ ID NO: 14.

There are principally three different approaches to targeting two or more pharmacological targets of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems can reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single compound. The design and validation of such multifunctional molecules are more complex and require substantial investigation into the optimal ratio of target activities in the molecule, but the unified pharmacokinetics may yield matched pharmacodynamic activities at the molecular targets. Multifunctional molecules may also be amenable to fixed dose combination with other drugs thereby combining three or even four pharmacologies in a single pill to produce further increments in efficacy.

Through diligent experimentation, the present inventor has invented a novel recombinant multi-functional fusion protein, which can attack tumors, via three mechanisms of actions, one to release CD24-Siglec-10 mediated immunosuppression, one to release the check on macrophages by SIRP-mediated inhibitory signals, the third to stimulate cancer cell killings by NK cells and/or macrophages.

The recombinant fusion protein of the present application comprises an anti-CD24 antibody or an antibody fragment thereof, with at least one paratope of the antibody or antibody fragment linked via a linker to an extracellular Ig-like domain of a signal-regulatory protein (SIRP) at the N-terminus of a heavy chain variable region or a light chain variable region constituting the paratope. The recombinant protein can bind to CD47, CD24 and FcR simultaneously, i) blocking the interaction of CD24s on cancer cells with Siglec-10s on immune cells and thus releasing CD24-Siglec-10 mediated immunosuppression; ii) blocking the interaction of CD47s on cancer cells with SIRPs on macrophages and thus releasing the check on macrophages by SIRP-mediated inhibitory signals; and iii) binding Fc portion of the antibody to FcRs on NK cells and/or macrophages to stimulate cancer cell killings by NK cells and/or macrophages. In an embodiment, one paratope of the anti-CD24 antibody or antibody fragment thereof is linked via a linker to an extracellular Ig-like domain of a signal-regulatory protein (SIRP) at the N-terminus of a heavy chain variable region or a light chain variable region constituting the paratope. In another embodiment, each paratope of the anti-CD24 antibody or antibody fragment thereof is linked via a linker to an extracellular Ig-like domain of a signal-regulatory protein (SIRP) at the N-terminus of a heavy chain variable region or a light chain variable region constituting the paratope. In one embodiment, each paratope of the anti-CD24 antibody or antibody fragment thereof is linked via a linker to an extracellular Ig-like domain of a signal-regulatory protein (SIRP) at the N-terminus of a heavy chain variable region constituting the paratope. In one embodiment, each paratope of the anti-CD24 antibody or antibody fragment thereof is linked via a linker to an extracellular Ig-like domain of a signal-regulatory protein (SIRP) at the N-terminus of a light chain variable region constituting the paratope. The recombinant fusion protein of the present application is small in size (150-180 kDa) and has a long half-life of 5-10 days.

The three main components contained in the recombinant fusion protein of the present application are the extracellular Ig-like domain of a signal-regulatory protein (SIRP), the linker, and the anti-CD24 antibody. A person of ordinary skills in the art will recognize that there are many design choices for selecting the above three components. Preferably, human-derived sequence is used in human cancer therapies, as the strong immunogenicity of the proteins or peptides from non-human animals may lead to allergy and other adverse effects. However, other animal proteins or peptides, humanized if appropriate, may also be used in the present application based on different application purposes.

Any extracellular Ig-like domain of any SIPR (SIRPα, SIRPβ, and SIRPγ) capable of binding with CD47 may be selected for construction of the recombinant fusion protein. In one embodiment, the signal-regulatory protein in the recombinant fusion protein is SIRPα, and the extracellular Ig-like domain of the signal-regulatory protein is the first extracellular Ig-like domain of SIRPα (SIRPαD1). In certain embodiments, SIRPαD1 is a SIRPαD1 mutant that contains an N→A mutation at position 80 of SEQ ID NO: 1 to remove a glycosylation site.

In one embodiment, the recombinant fusion protein may comprise SIRPαD1 having the amino acid sequence set forth in SEQ ID NO: 1. In another embodiment, the SIRPαD1 may comprise an amino acid sequence having at least 80%, 85%, 90%, 95%, 98% or 99% sequence identity to SEQ ID NO: 1, wherein the SIRPαD1 can bind to CD47s on the cell surface of cancer/tumor cells and block the interaction of CD47s with SIRPs on the cell surfaces of macrophages.

Linkers serve primarily as a spacer between the extracellular Ig-like domain of SIRP and the N-terminus of the heavy chain or light chain of an anti-CD24 antibody. The linker may be made up of amino acids linked together by peptide bonds, preferably from 5 to 30 amino acids, from 10 to 30 amino acids, from 10 to 20 amino acids, or 15 amino acids, linked by peptide bonds, wherein the amino acids are selected from the 20 naturally occurring amino acids. One or more of these amino acids may be glycosylated or deglycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines, particularly Glys, poly(Gly-Ala), and polyalanines. One exemplary suitable linker as shown in the Examples below is -(Gly-Ser)$_n$-, such as -(Gly-Gly-Gly-Gly-Ser)$_3$-(SEQ ID NO: 15).

Linkers may also be non-peptide linkers. For example, alkyl linkers such as —NH—, —(CH$_2$)s-C(O)—, wherein s=2-20 can be used. These alkyl linkers may further be substituted by any non-sterically hindering group such as lower alkyl (e.g., C$_{1-4}$) lower acyl, halogen (e.g., CI, Br), CN, NH$_2$, phenyl, etc.

In certain embodiments, the anti-CD24 antibody may be an isolated monoclonal IgG antibody comprising two heavy chains and two light chains, wherein each heavy chain may comprise a heavy chain variable region and a heavy chain constant region, and each light chain may comprise a light chain variable region and optionally a light chain constant region. The heavy chain variable region and the light chain variable region of the anti-CD24 antibody may comprise amino acid sequences set forth in i) SEQ ID NOs: 2 and 3, respectively, ii) SEQ ID NOs: 2 and 4, respectively, or iii) SEQ ID NOs: 5 and 6, respectively. The heavy chain constant region may comprise the amino acid sequence of SEQ ID NO: 13. The light chain constant region may comprise the amino acid sequence of SEQ ID NO: 14. The Fab portion (or paratope) of the anti-CD24 antibody may bind to CD24s on the cell surfaces of cancer/tumor cells to block the interaction of CD24s with Siglec-10s on the cell surfaces of immune cells such as T cells and thus release the CD24-Siglec-10 mediated immunosuppression, while the Fc portion of the anti-CD24 antibody may bind to FcRs on the cell surfaces of NK cells or macrophages to stimulate cancer cell killings by the NK cells or macrophages. In certain embodiments, the heavy chain variable region may comprise an amino acid sequence having at least 80%, 85%, 90%, 95%, 98% or 99% sequence identity to SEQ ID NOs: 2 or 5, and the heavy chain constant region may comprise an amino acid sequence having at least 80%, 85%, 90%, 95%, 98% or 99% sequence identity to SEQ ID NO: 13, wherein the anti-CD24 antibody is able to bind to CD24s on cancer/tumor cells and block the interaction of CD24s with Siglec-10s on immune cells such as T cells, and is also able to bind to FcRs on NK cells or macrophages and thus activate the NK cells or macrophages to kill the cancer cells. In certain embodiments, the light chain variable region may comprise an amino acid sequence having at least 80%, 85%, 90%, 95%, 98% or 99% sequence identity to SEQ ID NOs: 3, 4 or 6, wherein the anti-CD24 antibody is able to bind to CD24s on cancer/tumor cells and block the interaction of CD24s with Siglec-10s on immune cells such as T cells.

The term "antibody" as referred to herein includes whole antibodies of e.g., IgG, IgA, IgD, IgE and IgM, and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $CH_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody fragment" herein refers to a portion or fragment of an anti-CD24 antibody of the disclosure that retains the ability to specifically bind to CD24s, and optionally the ability to bind Fc receptors.

The heavy chain variable region CDRs and the light chain variable region CDRs in the antibody or antibody fragment thereof of the disclosure have been defined by the IMGT numbering system. However, as is well known in the art, CDR regions can also be determined by other systems such as Chothia, Kabat, AbM, or Contact numbering system/method, based on heavy chain/light chain variable region sequences.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "humanized antibody", as used herein, refers to an antibody from non-human species whose protein sequences have been modified to increase similarity to antibody variants produced naturally in humans.

The term "antibody dependent cellular cytotoxicity", "antibody dependent cell-mediated cytotoxicity" or "ADCC" refers to a mechanism of cell-mediated immune defense whereby an effector cell of the immune system actively lyses a target cell bound by antibodies such the anti-CD24 antibodies and SIRPα-containing molecules.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega, T-coffee, Kalign and MAFFT. When using such softwares, the default parameters, e.g. for gap penalty and extension penalty, are preferably used.

Also, the present application provides a polynucleotide molecule encoding the recombinant fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present application provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

In another aspect, the present disclosure provides a pharmaceutical composition comprising the recombinant fusion protein of the present application formulated together with a pharmaceutically acceptable excipient, or a pharmaceutically acceptable adjuvant. The composition may optionally contain one or more additional pharmaceutically active ingredients, such as another antibody or a drug. The pharmaceutical compositions of the application also can be administered in a combination therapy with, for example, another immune-stimulatory agent, anti-cancer agent, an anti-viral agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present application, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the application can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the fusion protein can be administered as a sustained release formulation, in which case less frequent administration is required.

For administration of the fusion protein, the dosage ranges from about 0.0001 to 100 mg/kg of the host body weight. An exemplary treatment regime entails administration twice per week.

A "therapeutically effective dosage" of a recombinant fusion protein of the application preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a recombinant fusion protein of the present application can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312, 335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475, 196); the disclosures of which are incorporated herein by reference.

In certain embodiments, the fusion protein of the application can be formulated to ensure proper distribution in vivo. For example, to ensure that the therapeutic fusion proteins of the application cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331.

A gene therapy in vivo is also envisioned wherein a nucleic acid molecule encoding the recombinant fusion protein of the present application, or a derivative thereof is introduced directly into the subject. For example, a nucleic acid sequence encoding a recombinant fusion protein of the present application is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present application is to provide a method for preparing the above recombinant fusion protein and the pharmaceutical composition comprising the same. In one embodiment, the method comprises (1) providing a protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present application is to provide a method of treating cancer using the pharmaceutical composition of the present application, comprising administrating an effective amount of the aforementioned pharmaceutical composition to the patients or subjects in need thereof. In one embodiment, the pharmaceutical composition is used to treat CD47 and/or CD24 overexpressing tumors or cancers, including but not limited to acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, renal cell carcinoma, cervical cancer, endometrial cancer, cholangiocarcinoma, stomach adenocarcinoma, and glioblastoma.

In one embodiment, the diseases related to over-expressions of CD47 and/or CD24 include, but are not limited to, Crohn's disease, allergic asthma, and rheumatoid arthritis.

The present application is now further described with the non-limiting examples below.

EXAMPLES

The exemplary recombinant proteins and anti-CD24 antibodies of the disclosure, whose structures were shown in FIG. 1, will be described below in further details.

IMM47C is an IgG antibody, comprising a heavy chain variable region of SEQ ID NO: 2, a heavy chain constant region of SEQ ID NO: 13, a light chain variable region of SEQ ID NO: 4, and a light chain constant region of SEQ ID NO: 14.

IMM47 is an IgG antibody, comprising a heavy chain variable region of SEQ ID NO: 2, a heavy chain constant region of SEQ ID NO: 13, a light chain variable region of SEQ ID NO: 3, and a light chain constant region of SEQ ID NO: 14.

IMM47H is an IgG antibody, comprising a heavy chain variable region of SEQ ID NO: 5, a heavy chain constant region of SEQ ID NO: 13, a light chain variable region of SEQ ID NO: 6, and a light chain constant region of SEQ ID NO: 14.

IMM4701C comprises a mutated SIRPαD1 (SEQ ID NO: 1) linked, via a linker (SEQ ID NO: 15), to the N-terminus of each heavy chain of IMM47C.

IMM4701 comprises a mutated SIRPαD1 (SEQ ID NO: 1) linked, via a linker (SEQ ID NO: 15), to the N-terminus of each heavy chain of IMM47.

IMM4702C comprises a mutated SIRPαD1 (SEQ ID NO: 1) linked, via a linker (SEQ ID NO: 15), to the N-terminus of each light chain of IMM47C.

IMM4702H comprises a mutated SIRPαD1 (SEQ ID NO: 1) linked, via a linker (SEQ ID NO: 15), to the N-terminus of each light chain of IMM47H.

IMM01, as described in US 2021/0024598A1, comprises two mutated SIRPαD1s (SEQ ID NO: 1) linked to a Fc dimer, whose monomer comprises the nucleic acid and amino acid sequences set forth in SEQ ID NOs: 33 and 32, respectively.

Example 1. Vector Construction and Protein Expression

The structures of IMM4701, IMM4701C, IMM4702C, IMM4702H, IMM47, IMM47C and IMM47H were shown in FIG. 1, and the full length coding sequences of the recombinant fusion proteins were designed artificially.

Specifically, for IMM4701C's long chain, 57 nucleotides encoding the signal peptide of mouse IgG1 heavy chain (SEQ ID NO: 34) were added to the 5' end of the coding sequence of the SIRPαD1-linker-anti-CD24 heavy chain (SEQ ID NO: 19), and a Kozak sequence (SEQ ID NO: 35) was added to the 5' end of the signal peptide sequence. Lastly, HindIII and NheI restriction sites were added to the 5' and 3' ends of the resulting sequence, respectively. For IMM4701C's short chain, the same signal sequence as well as the Kozak sequence was added to the 5' end of the anti-CD24 light chain coding sequence (SEQ ID NO: 21), and HindIII and XbaI restriction sites were added to the 5' and 3' ends of the resulting sequence, respectively. The sequences were synthesized by GenScript and cloned into pMac-H and pMac-L vectors, respectively.

For IMM4701's long chain, 57 nucleotides encoding the signal peptide of mouse IgG1 heavy chain (SEQ ID NO: 34) were added to the 5' end of the coding sequence of the SIRPαD1-linker-anti-CD24 heavy chain (SEQ ID NO: 19), and a Kozak sequence (SEQ ID NO: 35) was added to the 5' end of the signal peptide sequence. Lastly, HindIII and NheI restriction sites were added to the 5' and 3' ends of the resulting sequence, respectively. For IMM4701's short chain, the same signal sequence as well as the Kozak sequence was added to the 5' end of the anti-CD24 light chain coding sequence (SEQ ID NO: 23), and HindIII and XbaI restriction sites were added to the 5' and 3' ends of the resulting sequence, respectively. The sequences were synthesized by GenScript and cloned into pMac-H and pMac-L vectors, respectively.

For IMM4702C's long chain, 57 nucleotides encoding the signal peptide of mouse IgG1 heavy chain (SEQ ID NO: 34) were added to the 5' end of the coding sequence of the anti-CD24 heavy chain (SEQ ID NO: 25), and a Kozak sequence (SEQ ID NO: 35) was added to the 5' end of the signal peptide sequence. Lastly, HindIII and NheI restriction sites were added to the 5' and 3' ends of the resulting sequence, respectively. For IMM4702C's short chain, the same signal sequence as well as the Kozak sequence was added to the 5' end of the SIRPαD1-linker-anti-CD24 light chain coding sequence (SEQ ID NO: 27), and HindIII and XbaI restriction sites were added to the 5' and 3' ends of the resulting sequence, respectively. The sequences were synthesized by GenScript and cloned into pMac-H and pMac-L vectors, respectively.

For IMM4702H's long chain, 57 nucleotides encoding the signal peptide of mouse IgG1 heavy chain (SEQ ID NO: 34) were added to the 5' end of the coding sequence of the anti-CD24 heavy chain (SEQ ID NO: 29), and a Kozak sequence (SEQ ID NO: 35) was added to the 5' end of the signal peptide sequence. Lastly, HindIII and NheI restriction sites were added to the 5' and 3' ends of the resulting sequence, respectively. For IMM4702H's short chain, the same signal sequence as well as the Kozak sequence was added to the 5' end of the SIRPαD1-linker-anti-CD24 light chain coding sequence (SEQ ID NO: 31), and HindIII and XbaI restriction sites were added to the 5' and 3' ends of the resulting sequence, respectively. The sequences were synthesized by GenScript and cloned into pMac-H and pMac-L vectors, respectively.

These recombinant fusion proteins of the disclosure and the anti-CD24 antibodies were expressed using CHO-S cells. Briefly, CHO-S cells were seeded at a density of $1 \times 10^6$ cells/ml in TransFx-CTMCHO Transient transfection Medium (Hyclone) containing 6 mM glutamine one day before transient transfection. The heavy/long chain and light/short chain expression vectors, at a mass ratio of 1:1 and a total DNA amount of 1 μg/ml, were added to OPTI-MEM medium (Gibco) whose volume was 1/20 of that of the TransFx-CTMCHO Transient transfection Medium as used. PEI (polyethylenimine, MW 40,000, polysciences) at 1 mg/ml was added to OPTI-MEM medium (Gibco) whose volume was 1/20 of that of the TransFx-CTMCHO Transient transfection Medium as used. The PEI dilution was slowly added to, mixed and incubated at room temperature for 20 min with the diluted DNAs, at a PEI:DNA mass ratio of 4:1. Then, the DNA/PEI mixture was added to the cell cultures, and the cells were incubated in a 37° C. and 5% $CO_2$ cell culture incubator with shaking at 110 rpm. Transfection enhancer (1 mM sodium butyrate, 0.25% V/V DMSO) was added two days later, and the temperature was reduced to 33° C. When the cell viability dropped to ~50%, the cell culture supernatant was harvested from the bioreactor by centrifugation at 3000 rpm for 5 min, and subjected to protein purification using Protein A chromatography.

Example 2. Exemplary Recombinant Fusion Protein Bound to CD47s on Jurkat Cells

Jurkat cells (naturally expressing CD47) of 100 μl at a cell density of $1 \times 10^6$/ml were incubated with 100 μl serially diluted IMM4701, IMM4701C, IMM4702C, IMM4702H, IMM01 and IMM47 (3-fold dilution, starting at 30 μg/ml), respectively, at 4° C. for 1 h. Cells were washed with cold PBS twice, and then incubated with 100 μl FITC-conjugated secondary antibody against human IgG-Fc (Cat #F9512, Sigma) for 45 min. Cells were washed twice and re-suspended in 200 μl PBS. Then, the cells were subject to FACS analysis using a flow cytometer (Merck Millipore, Guava® easyCyte 5HT).

Figure 2A:
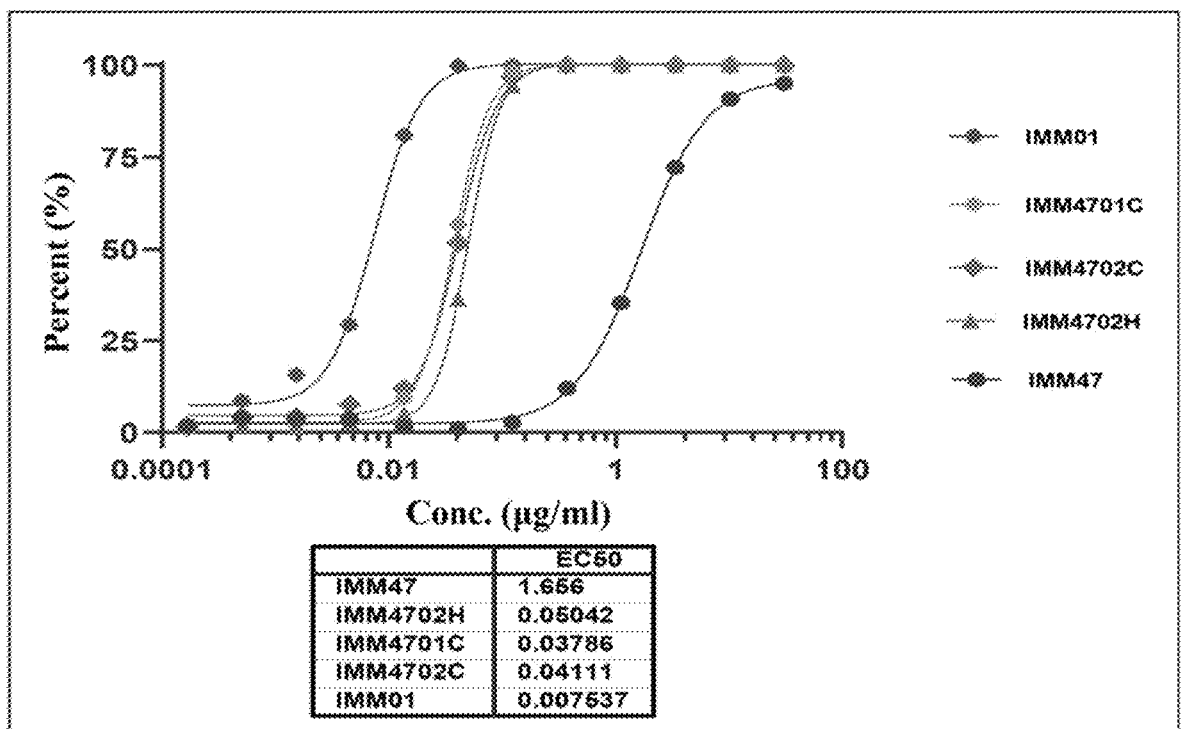
FIGS. 2A and 2B show the binding activities of IMM4701C (A and B), IMM4701 (B), IMM4702C (A) and IMM4702H (A) to CD47s on Jurkat human T cell leukemia cells. IMM01, used as the positive control, was described in US 2021/0024598 A1 and comprises two mutated SIRPαD1s (SEQ ID NO: 1) linked to an Fc dimer fragment, whose monomer has the nucleic acid and amino acid sequences of SEQ ID NO: 33 and SEQ ID NO: 32, respectively. The anti-CD24 antibody IMM47 was used as the negative control.
Figure 2B:
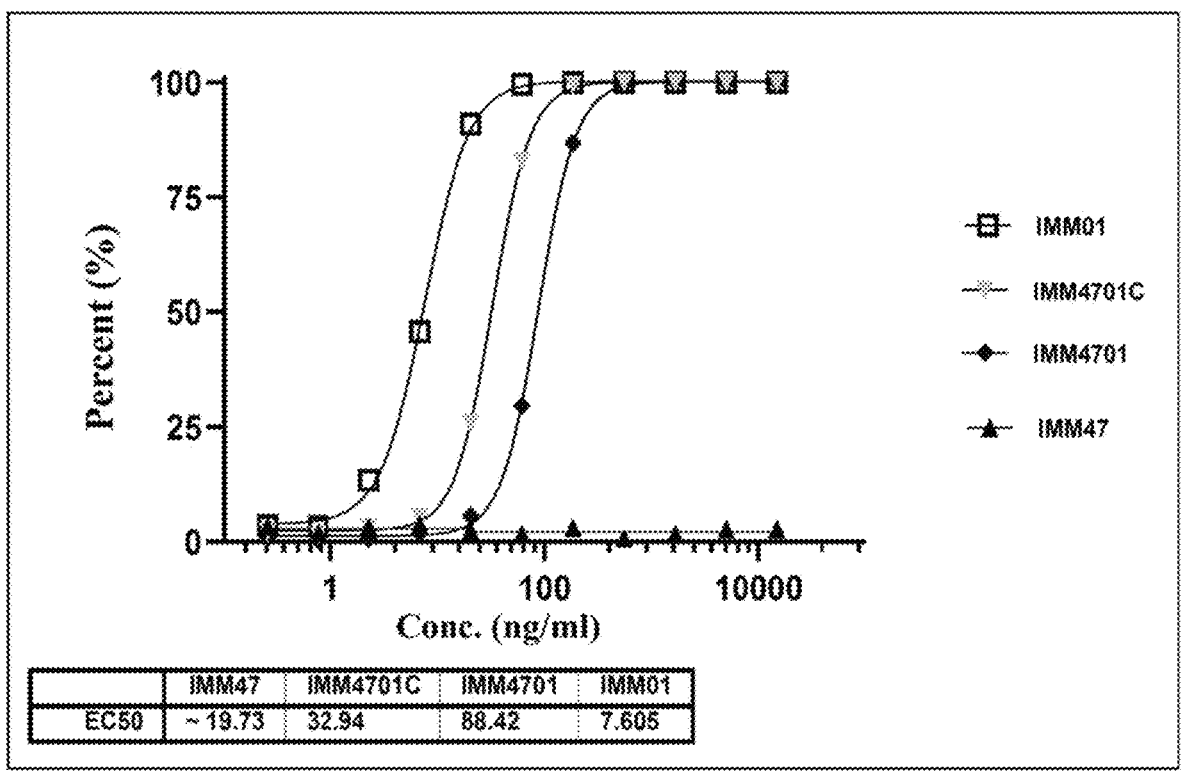

As shown in FIGS. 2A and 2B, IMM4701, IMM4701C, IMM4702C and IMM4702H bound to CD47s on Jurkat cells, with a bit inferior activities than the monospecific CD47 binding molecule IMM01.

Example 3. Exemplary Recombinant Fusion Protein Bound to CD24+ CD47+ MCF-7 Cells CD24+CD47+ MCF-7 cells of 100 μl at a cell density of $1 \times 10^6$/ml were incubated with 100 μl serially diluted IMM4701, IMM4701C, IMM4702C, IMM4702H, IMM01 and IMM47H (3-fold dilution, starting at 30 μg/ml), respectively, at 4° C. for 1 h, hIgG-Fc was used as the negative control. Cells were washed with cold PBS twice, and then incubated with 100 μl FITC-conjugated secondary antibody against human IgG-Fc (Cat #F9512, Sigma) for 45 min. Cells were washed twice and re-suspended in 200 μl PBS. Then, the cells were subject to FACS analysis using a flow cytometer (Merck Millipore, Guava® easyCyte 5HT).

Figure 3A:
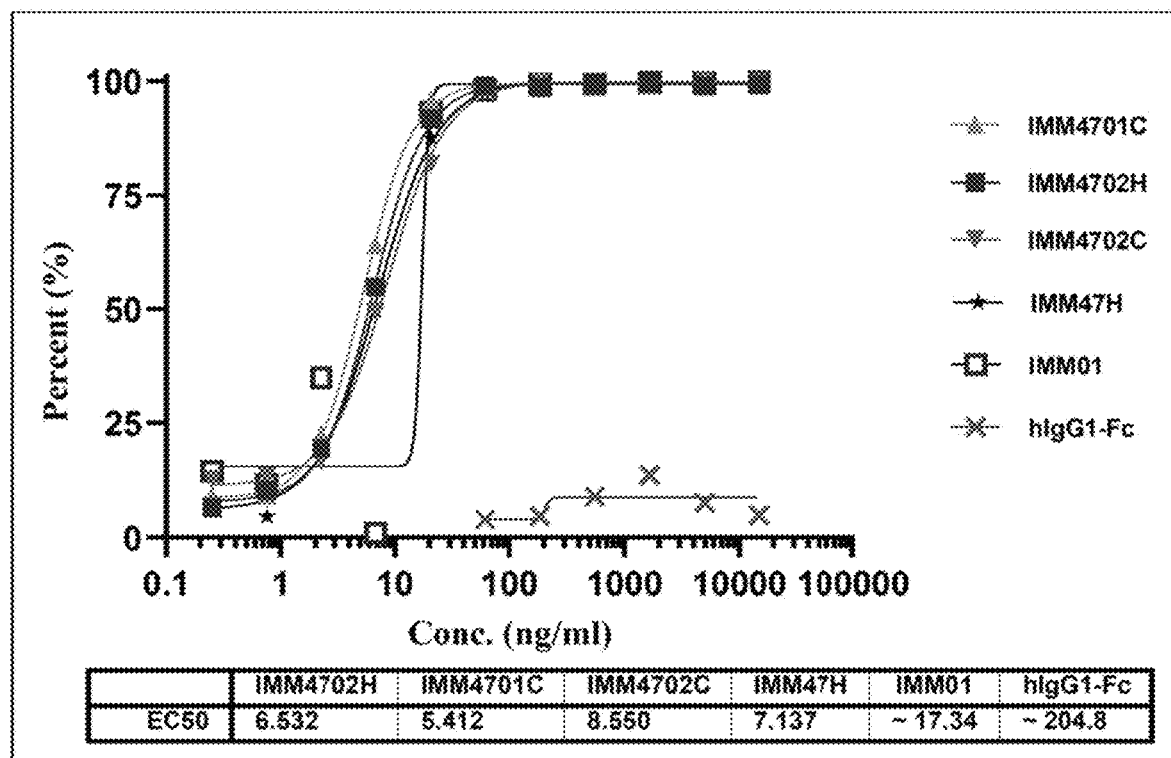
FIGS. 3A and 3B show the binding activities of IMM4701C (A and B), IMM4701 (B), IMM4702C (A) and IMM4702H (A) to $CD47^+CD24^+$ MCF-7 human breast cancer cells. IMM01 and IMM47H were used as positive controls, and hIgG-Fc was used as the negative control.
Figure 3B:
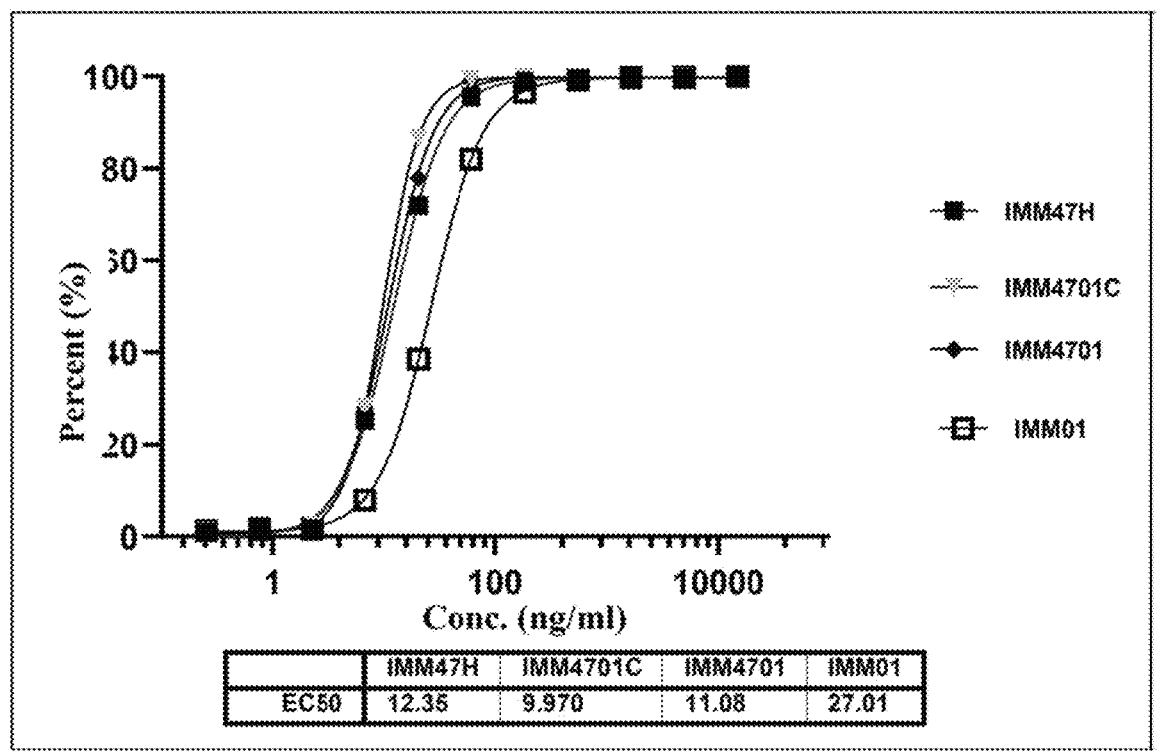

As shown in FIGS. 3A and 3B, the binding capabilities of IMM4701, IMM4701C, IMM4702C and IMM4702H to CD24+ CD47+ MCF-7 cells were comparable to that of the anti-CD24 antibody IMM47H and a bit higher than that of IMM01.

Example 4. Exemplary Recombinant Fusion Protein Bound to CD24+ CD47+ REH Cells

CD24+CD47+ REH cells of 100 μl at a cell density of $1 \times 10^6$/ml were incubated with 100 μl serially diluted IMM4701C, IMM4702C, IMM4702H, IMM01 and IMM47H (3-fold dilution, starting at 30 μg/ml), respectively, at 4° C. for 1 h, hIgG-Fc was used as the negative control. Cells were washed with cold PBS twice, and then incubated with 100 μl FITC-conjugated secondary antibody against human IgG-Fc (Cat #F9512, Sigma) for 45 min. Cells were washed twice and re-suspended in 200 μl PBS. Then, the cells were subject to FACS analysis using a flow cytometer (Merck Millipore, Guava® easyCyte 5HT).

Figure 4:
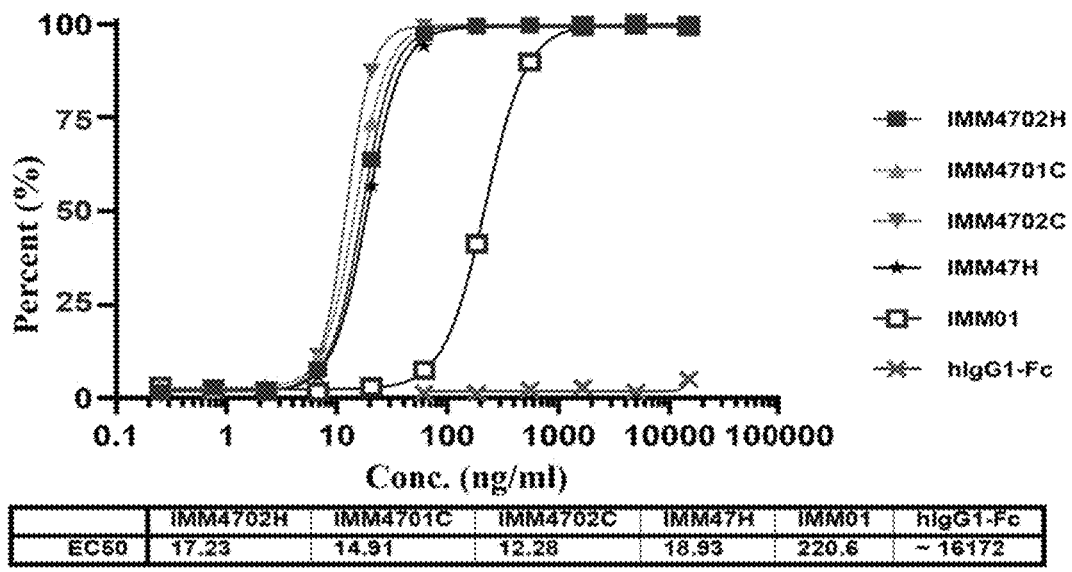
FIG. 4 shows the binding activities of IMM4701C, IMM4702C and IMM4702H to $CD47^+CD24^+$ REH human acute lymphocytic leukemia cells. IMM01 and IMM47H were used as positive controls, and hIgG-Fc was used as the negative control.

As shown in FIG. 4, the binding capabilities of IMM4701C, IMM4702C and IMM4702H to CD24+ CD47+ REH cells were comparable to that of IMM47H and a bit better than that of IMM01.

Example 5. Exemplary Recombinant Fusion Protein Inhibited CD47-SIRPα Interaction SIRPα-mFc (wild type human SIRPα conjugated with mouse IgG1 Fc, SEQ ID NO: 36) of 50 μl at 3 μg/ml was mixed with 50 μl serially diluted IMM4701, IMM4701C, IMM4702C, IMM4702H and IMM01 (3-fold dilution, starting at 30 μg/ml), respectively, and hIgG1-Fc was used as the negative control. The resultant mixtures were added to the wells of a 96-well plate each containing 50 μl $1 \times 10^6$/ml CD47+CD24+ MCF-7 cells, and the plate was incubated at 4° C. for 45 min. Cells were washed with PBS and incubated with 100 μl PE-conjugated secondary antibody against mouse IgG-Fc (Cat #405307, Biolegend) for 45 min. Cells were washed twice, re-suspended in 200 μl PBS, and subject to FACS analysis.

Figure 5:
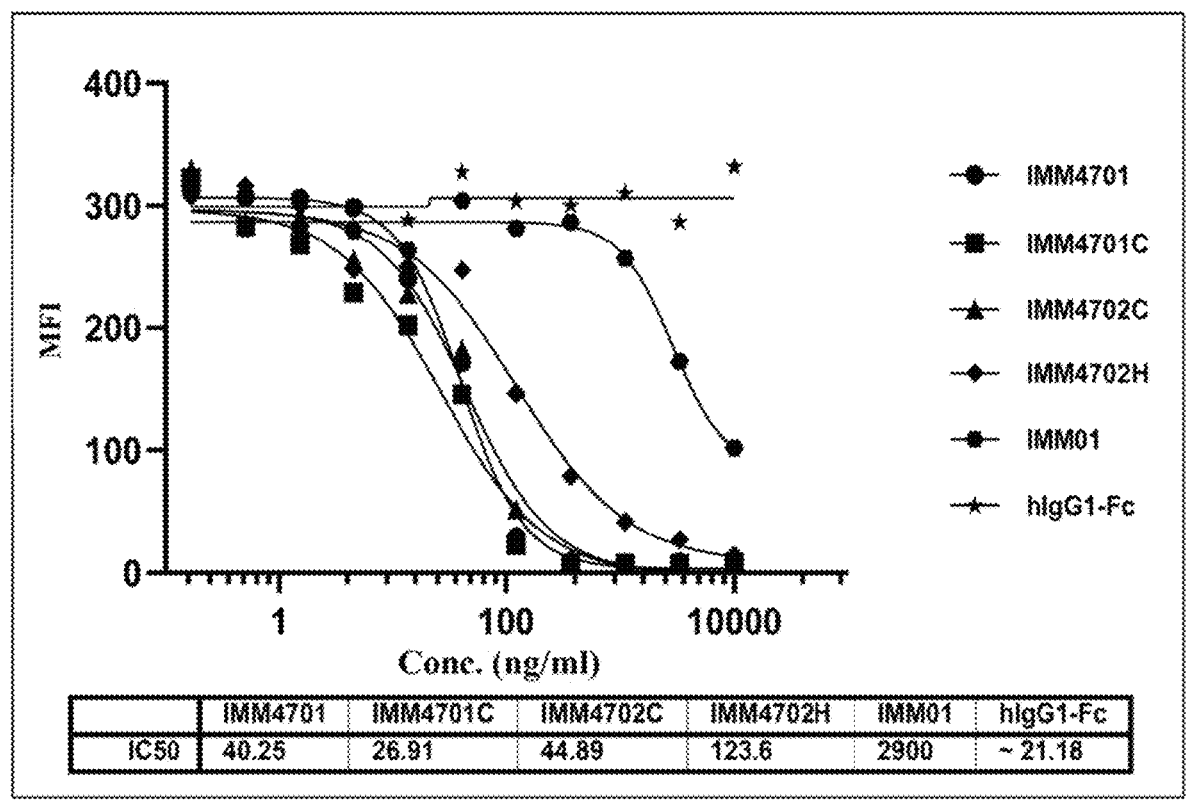
FIG. 5 shows the capabilities of IMM4701, IMM4701C, IMM4702C, and IMM4702H to block binding of SIRPα-Fc with CD47s on MCF-7 human breast cancer cells. IMM01 was used as the positive control, and hIgG-Fc was used as the negative control.

As shown in FIG. 5, the bispecific molecules against both CD24 and CD47, i.e., IMM4701, IMM4701C, IMM4702C and IMM4702H, when incubated with CD24+ CD47+ cells, showed higher inhibitory effects on SIRPα-CD47 interaction than IMM01.

Example 6. Exemplary Recombinant Fusion Protein Induced High Antibody-Dependent Cell-Mediated Cytotoxicity (ADCC) Against CD24+ CD47+ MCF-7 Cells CFSE (Cat #21888-25 mg, Sigma) at 1 mM was 1:500 diluted and used to label MCF-7 cells.

The CFSE-labeled MCF-7 cells, as the target cells, of 50 μl at $6 \times 10^5$/ml, were mixed at a 2:1 effector:target ratio with 100 μl $6 \times 10^5$/ml NK92MI cells stably expressing FcγRIIIa (158V), as the effector cells. The mixed cells were cultured for 4 hours at 37° C. under 5% $CO_2$ with 50 μl serially diluted IMM47C, IMM4701 and IMM4701C (3-fold dilution, starting at 1000 ng/ml), respectively, hIgG-Fc was used as the negative control. Then cell cultures were added with propidium iodide (PI) (Cat #P4170, Sigma) at a concentration of 5 μg/ml, and then subjected to FACS analysis for PI signals. Percentage of cell lysis caused by ADCC was calculated based on the following formula:

% Lysis=(% PI Positive Target Cells treated with IMM47C,IMM4701 or IMM4701C−% PI Positive Target Cells treated with negative control)/(100−% PI Positive Target Cells treated with negative control)*100

Figure 6:
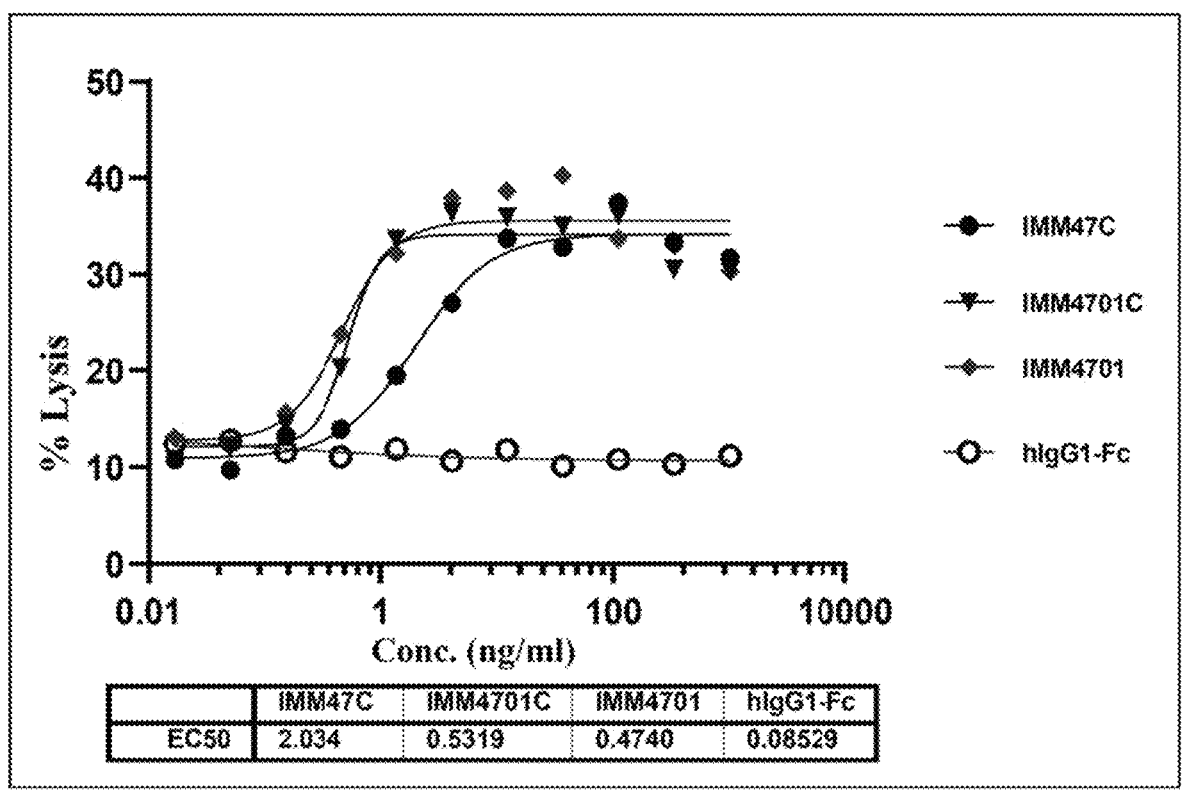
FIG. 6 shows the capabilities of IMM4701C and IMM4701 to induce antibody-dependent cellular cytotoxicity (ADCC) against $CD47^+CD24^+$ MCF-7 human breast cancer cells. IMM47C having ADCC activity was used as the positive control, and hIgG1-Fc was used as the negative control.

According to FIG. 6, IMM4701 and IMM4701C induced higher ADCC against CD24+ CD47+ MCF-7 cells than IMM47C.

Example 7. Exemplary Recombinant Fusion Protein Induced High Antibody-Dependent Cell-Mediated Cytotoxicity (ADCC) Against CD24+ CD47+ REH Cells CFSE (Cat #21888-25 mg, Sigma) at 1 mM was 1:500 diluted and used to label REH cells.

The CFSE-labeled REH cells, as the target cells, of 50 μl at 6×10⁵/ml, were mixed at a 2:1 effector:target ratio with 100 μl 6×10⁵/ml NK92MI cells stably expressing FcγRIIIa (158V), as the effector cells. The mixed cells were cultured for 4 hours at 37° C. under 5% $CO_2$ with 50 μl serially diluted IMM47C, IMM4701C, IMM4702C and IMM4702H (3-fold dilution, starting at 1000 ng/ml), respectively, and hIgG-Fc was used as the negative control. Then cell cultures were added with propidium iodide (PI) (Cat #P4170, Sigma) at a concentration of 5 μg/ml, and then subjected to FACS analysis for PI signals. Percentage of cell lysis caused by ADCC was calculated based on the following formula:

% Lysis=(% PI Positive Target Cells treated with IMM47C, IMM4701C, IMM4702C or IMM4702H−% PI Positive Target Cells treated with negative control)/(100−% PI Positive Target Cells treated with negative control)*100

Figure 7:
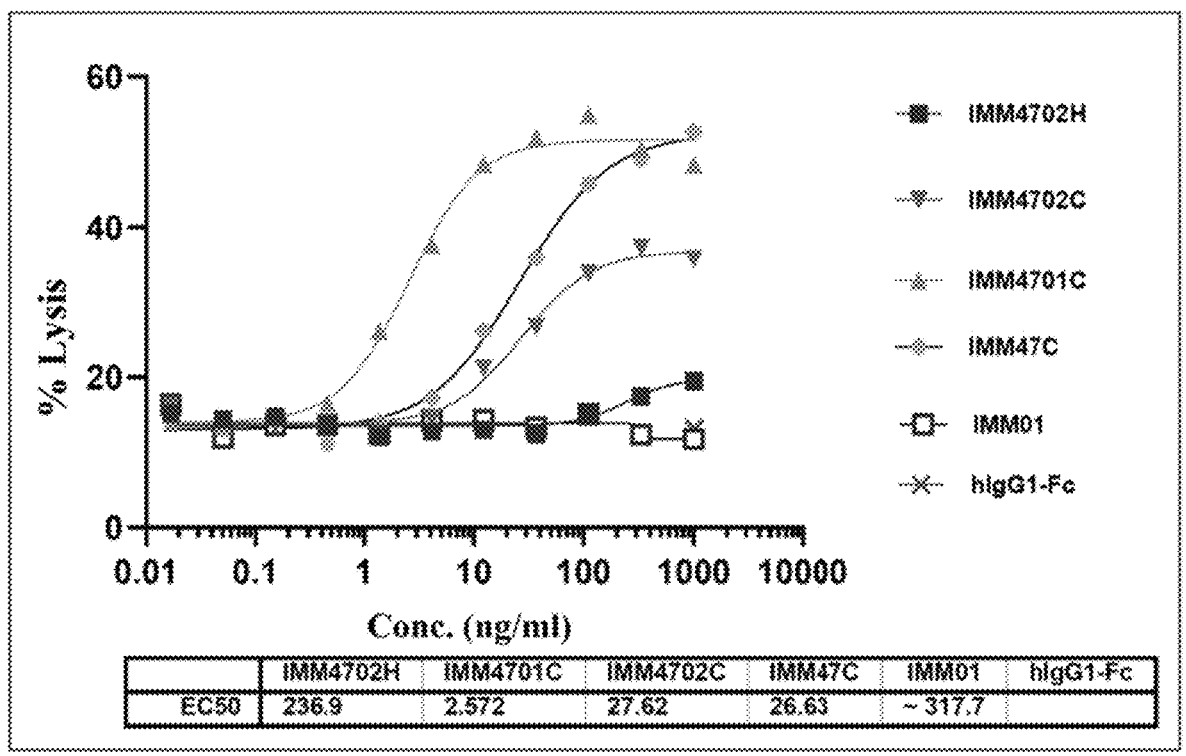
FIG. 7 shows the capabilities of IMM4701C, IMM4702C and IMM4702H to induce antibody-dependent cellular cytotoxicity (ADCC) against $CD47^+CD24^+$ REH human acute lymphocytic leukemia cells. IMM47C having ADCC activity was used as the positive control, hIgG1-Fc and IMM01 having little ADCC activity were used as the negative controls.

According to FIG. 7, IMM4701C induced higher ADCC against CD24+ CD47+ REH cells than IMM47C.

Example 8. Exemplary Recombinant Fusion Protein Induced High Antibody-Dependent Cell-Mediated Cytotoxicity (ADCC) Against CD24+ MC38-hCD24 Cells CFSE (Cat #21888-25 mg, Sigma) at 1 mM was 1:500 diluted and used to label MC38-hCD24 cells.

The CFSE-labeled MC38-hCD24 cells, as the target cells, of 50 μl at 6×10⁵/ml, were mixed at a 2:1 effector:target ratio with 100 μl 6×10⁵/ml NK92MI cells stably expressing FcγRIIIa (158V), as the effector cells. The mixed cells were cultured for 4 hours at 37° C. under 5% $CO_2$ with 50 μl serially diluted IMM47, IMM4701C and IMM4701 (3-fold dilution, starting at 1000 ng/ml), respectively, and hIgG-Fc was used as the negative control. Then cell cultures were added with propidium iodide (PI) (Cat #P4170, Sigma) at a concentration of 5 μg/ml, and then subjected to FACS analysis for PI signals. Percentage of cell lysis caused by ADCC was calculated based on the following formula:

% Lysis=(% PI Positive Target Cells treated with IMM4701C,IMM4701−% PI Positive Target Cells treated with negative control)/(100−% PI Positive Target Cells treated with negative control)*100

Figure 8:
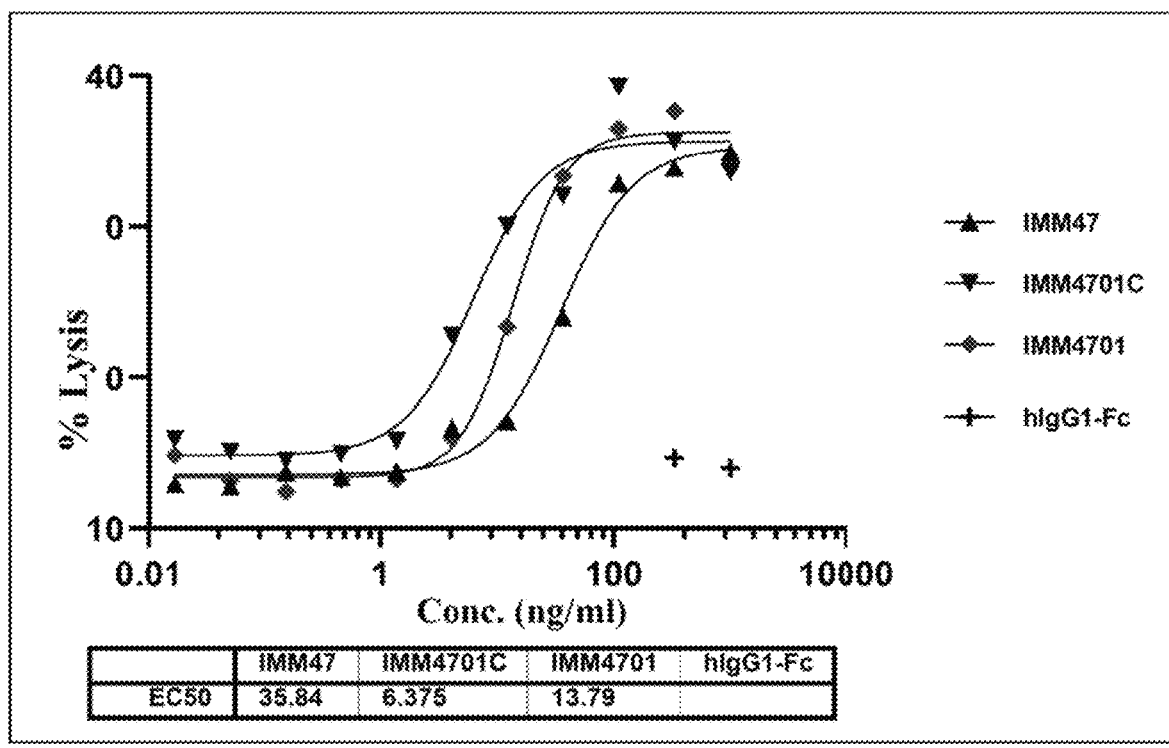
FIG. 8 shows the capabilities of IMM4701C and IMM4701 to induce antibody-dependent cellular cytotoxicity (ADCC) against MC38-hCD24 murine colon adenocarcinoma cells engineered to express human CD24s. IMM47 having ADCC activity was used as the positive control, and hIgG1-Fc was used as the negative control.

According to FIG. 8, IMM4701C and IMM4701 induced higher ADCC against human CD24 expressing-MC38-hCD24 cells than the anti-CD24 antibody IMM47.

Example 9. Exemplary Recombinant Fusion Protein Showed Potent Anti-Tumor Activity Forty 6-8-week-old SCID mice each had a 0.36 mg beta-estradiol delayed-release tablet embedded at the left back, 3 days before subcutaneous injection of MCF-7 human breast cancer cells, 1×10⁷ cells per mouse, at the right flank. When tumor volumes reached 100-150 mm³, mice were randomly allocated into five groups with 8 mice per group, and this day was designated as Day 0. From that day on, mice were respectively given intraperitoneal injection of PBS, IMM47C (2.5 mg/kg), IMM01 (2.5 mg/kg), IMM4701C (3 mg/kg), and IMM01+IMM47C (2.5 mg/kg+ 2.5 mg/kg), for 4 weeks, twice per week. Administration was stopped at the end of week 4 and mice were observed till termination of experiment when the average tumor volume in the PBS group reached 3000 mm³. Tumor sizes and body weights were measured every 3-4 days.

The tumor volume (V) was calculated as (length×width²)/2. Tumor growth inhibition rate (TGI) was calculated by the formula: TGI (%)=(1−tumor volume change in administration group/tumor volume change in vehicle control group)× 100%.

The test regime and results were summarized in Table 1.

TABLE 1

Anti-tumor effect of IMM4701C and other agents

| Group | Drug | Animal# | Dose (mg/kg) | Treatment | TGI | P value |
|---|---|---|---|---|---|---|
| 1 | PBS | 8 | n/a | i.p.b.w. × 4 | | |
| 2 | IMM01 | 8 | 2.5 | i.p.b.w. × 4 | 17.19% | 0.375 |
| 3 | IMM47C | 8 | 2.5 | i.p.b.w. × 4 | 37.30% | 0.009 |
| 4 | IMM4701C | 8 | 3.0 | i.p.b.w. × 4 | 122.32% | 0.001 |
| 5 | IMM01 + IMM47C | 8 | 2.5 + 2.5 | i.p.b.w. × 4 | 92.22% | 0.001 |

On Day 28, the average tumor volume of mice in Group 1 (PBS) was 646.87 mm³. Compared to the vehicle control group, both IMM47C and IMM01 treatments slowed tumor growth rate, but didn't exhibit significant tumor suppressor effects. These two groups had average tumor sizes at 463.26 mm³ (T/C=71.60%, TGI=37.30%, p=0.009) and 562.24 mm³ (T/C=86.92%, TGI=17.19%, p=0.375), respectively, on Day 28. IMM4701C and IMM47C+IMM01 administrations showed significant tumor suppression effects, the mice in the two groups respectively had tumor sizes at 44.61 mm³ (T/C=6.89%, TGI=122.32%, p=0.001) and 192.63 mm³ (T/C=29.81%, TGI=92.22%, p=0.001), respectively, on Day 28.

Figure 9:
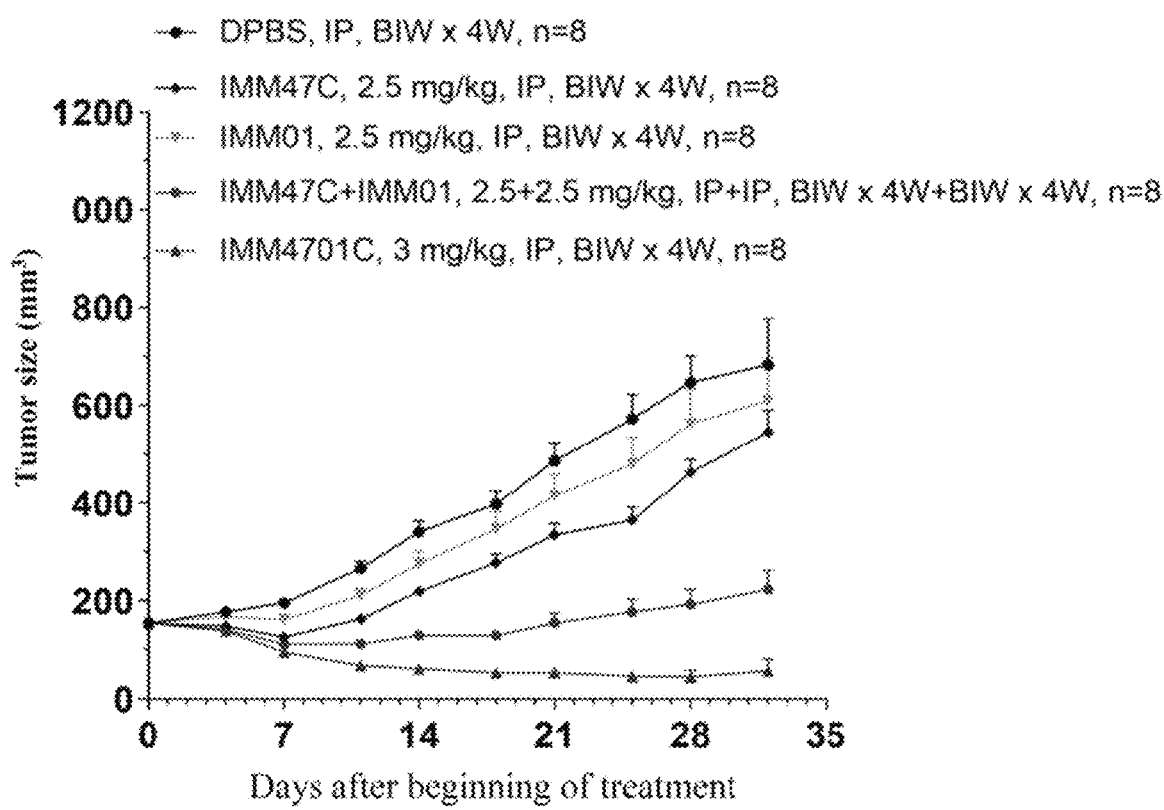
FIG. 9 shows the in vivo anti-tumor efficacy of IMM4701C in CB17-SCID mice bearing CD24+CD47+ MCF-7 human breast cancer cell derived xenografts. DPBS was used as the vehicle control, IMM47C and IMM01 were used as the positive controls.

It can be seen from Table 1 and FIG. 9 that IMM4701C functioned in an efficient and effective manner and produced greater in vivo anti-tumor efficacy, with the overall tumor inhibition effect being even better than the IMM47C and IMM01 combination treatment.

| Description | Sequence/SEQ ID NO. |
|---|---|
| first extracellular Ig-like domain of SIRPα with mutation (SIRPαD1) | EEELQVIQPDKSVSVAAGESAILHCTVTSLIPVGPIQWFRGAGPARELIYNQKEGHFPRVTTVS ESTKRENMDFSISISAITPADAGTYYCVKFRKGSPDTEFKSGAGTELSVRAKPSAPVVSGP (SEQ ID NO: 1) |
| IMM47 and IMM47C's heavy chain variable region | DVQLQESGPDLVKPSQSLSLTCTVTGYSITSGYSWHWIRQFPGNKLEWMGYIHYSGSTKYNP SLKSRISITRDTSKNQFFLQLNSVTTEDTATYFCARGADYALDYWGQRTSVTVSS (SEQ ID NO: 2) |
| IMM47's light chain variable region | DIQMTQSPSSLSASVGDRVTITCKSSQSLLYSSNQKNYLAWYQQKPGKAPKLLIYWASTRES GVPSRFSGSGSGTDFTLTISSLQPEDFATYYCQQNFIYPLTFGGGTKVELK (SEQ ID NO: 3) |
| IMM47C's light chain variable region | DIVMSQSPSSLAVSVGEKVTMSCKSSQSLLYSSNQKNYLAWYQQKPGHSPKLLIYWASTRES GVPDRFTGSGSGTDFTLTISSVKAEDLAVYYCQQNFIYPLTFGAGTKLELK (SEQ ID NO: 4) |
| IMM47H's heavy chain variable region | DVQLQESGPGLVKPSETLSLTCTVSGYSITSGYSWHWIRQPPGKGLEWIGYIHYSGSTKYNPS LKSRVTISVDTSKNQFSLKLSSVTAADTAVYYCARGADYALDYWGQRTSVTVSS (SEQ ID NO: 5) |
| IMM47H's light chain variable region | DIVMTQSPDSLAVSLGERATINCKSSQSLLYSSNQKNYLAWYQQKPGQPPKLLIYWASTRES GVPDRFSGSGSGTDFTLTISSLQAEDVAVYYCQQNFIYPLTFGGGTKVELK (SEQ ID NO: 6) |
| IMM47, IMM47C and IMM47H's heavy chain CDR1 (HV-CDR-1) | GYSITSGYS (SEQ ID NO: 7) |
| IMM47, IMM47C and IMM47H's heavy chain CDR2 (HV-CDR-2) | IHYSGST (SEQ ID NO: 8) |
| IMM47, IMM47C and IMM47H's heavy chain CDR3 (HV-CDR-3) | ARGADYALDY (SEQ ID NO: 9) |
| IMM47, IMM47C and IMM47H's light chain CDR1 (LV-CDR-1) | QSLLYSSNQKNY (SEQ ID NO: 10) |
| IMM47, IMM47C and IMM47H's light chain CDR2 (LV-CDR-2) | WAS (SEQ ID NO: 11) |
| IMM47, IMM47C and IMM47H's light chain CDR3 (LV-CDR-3) | QQNFIYPLT (SEQ ID NO: 12) |
| IMM47, IMM47C and IMM47H's heavy chain constant region | ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLGGPSVFLFP PKPKDTLMISRTPEVTCVVVDVSHEDPEVKFNWYVDGVEVHNAKTKPREEQYNATYRVVSV LTVLHQDWLNGKEYKCKVSNKALPAPIAATISKAKGQPREPQVYTLPPSREEMTKNQVSLTC LVKGFYPSDIAVEWESNGQPENNYKTTPPVLDSDGSFFLYSKLTVDKSRWQQGNVFSCSVM HEALHNHYTQKSLSLSPGK (SEQ ID NO: 13) |
| IMM47, IMM47C and IMM47H's light chain constant region | RTVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC (SEQ ID NO: 14) |
| Linker | GGGGSGGGGSGGGGS (SEQ ID NO: 15) |
| | GGGGSGGGGS (SEQ ID NO: 16) |
| | GGGGSGGGGSGGGGSGGGGS (SEQ ID NO: 17) |
| IMM4701C's long chain (SIRPαD1-linker-IMM47C's heavy chain) | EEELQVIQPDKSVSVAAGESAILHCTVTSLIPVGPIQWFRGAGPARELIYNQKEGHFPRVTTVS ESTKRENMDFSISISAITPADAGTYYCVKFRKGSPDTEFKSGAGTELSVRAKPSAPVVSGPGG GGSGGGGSGGGGSDVQLQESGPDLVKPSQSLSLTCTVTGYSITSGYSWHWIRQFPGNKLEW MGYIHYSGSTKYNPSLKSRISITRDTSKNQFFLQLNSVTTEDTATYFCARGADYALDYWGQR TSVTVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCPAPELLG GPSVFLFPPKPKDTLMISRTPEVTCVVVDVSHEDPEVKFNWYVDGVEVHNAKTKPREEQYN ATYRVVSVLTVLHQDWLNGKEYKCKVSNKALPAPIAATISKAKGQPREPQVYTLPPSREEMT KNQVSLTCLVKGFYPSDIAVEWESNGQPENNYKTTPPVLDSDGSFFLYSKLTVDKSRWQQG NVFSCSVMHEALHNHYTQKSLSLSPGK (SEQ ID NO: 18) ATGGGATGGTCATGTATCATCCTTTTTCTGGTAGCAACTGCAACTGGAGTACATTCAGAG GAGGAGCTGCAGGTGATTCAGCCTGACAAGTCCGTATCAGTTGCAGCTGGAGAGTCGGC CATTCTGCACTGCACTGTGACCTCCCTGATCCCTGTGGGGCCCATCCAGTGGTTCAGAGG |

| Description |
|---|
| Sequence/SEQ ID NO. |

AGCTGGACCAGCCCGGGAATTAATCTACAATCAAAAAGAAGGCCACTTCCCCCGGGTAA
CAACTGTTTCAGAGTCCACAAAGAGAGAAAACATGGACTTTTCCATCAGCATCAGTGCC
ATCACCCCAGCAGATGCCGGCACCTACTACTGTGTGAAGTTCCGGAAAGGGAGCCCTGA
CACGGAGTTTAAGTCTGGAGCAGGCACTGAGCTGTCTGTGCGTGCCAAACCCTCTGCCCC
CGTGGTATCGGGCCCTGGCGGCGGTGGGAGCGGCGGCGGTGGGAGCGGCGGCGGGGGC
TCGGATGTGCAGCTTCAGGAGTCAGGACCTGACCTGGTGAAACCTTCTCAGTCACTTTCA
CTCACCTGCACTGTCACTGGCTACTCCATCACCAGTGGTTATAGCTGGCACTGGATCCGG
CAGTTTCCAGGAAACAAACTGGAATGGATGGGCTACATACACTATAGTGGTAGCACTAA
GTACAACCCATCTCTCAAAAGTCGAATCTCTATCACTCGAGACACATCCAAGAACCAGTT
CTTCCTGCAGTTGAATTCTGTGACTACTGAGGACACAGCCACATATTTCTGTGCAAGAGG
CGCGGACTATGCTTTGGACTACTGGGGTCAACGAACCTCAGTCACCGTCTCCTCAGCTAG
CACCAAGGGCCCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAGAGTTGAGCCCAAA
TCTTGTGACAAAACTCACACATGCCCACCGTGCCCAGCACCTGAACTCCTGGGGGGACCG
TCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTA
TGTGGACGGCGTGGAGGTGCATAATGCCAAGACAAAGCCGCGGGAGGAGCAGTACAAC
GCCACGTACCGTGTGGTCAGCGTCCTCACCGTCCTGCACCAAGACTGGCTGAATGGCAAG
GAGTACAAGTGCAAGGTCTCCAACAAAGCCCTCCCAGCCCCCATCGCCGCAACCATCTCC
AAAGCCAAAGGGCAGCCCCGAGAACCACAGGTGTACACCCTGCCCCCATCCCGGGAGGA
GATGACCAAGAACCAAGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCC
GTGCTGGACTCCGACGGCTCCTTCTTCCTCTATTCCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGCAAATGA (SEQ ID NO: 19)

IMM4701C's short chain (IMM47C's light chain)
DIVMSQSPSSLAVSVGEKVTMSCKSSQSLLYSSNQKNYLAWYQQKPGHSPKLLIYWASTRES
GVPDRFTGSGSGTDFTLTISSVKAEDLAVYYCQQNFIYPLTFGAGTKLELKRTVAAPSVFIFPP
SDEQLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO: 20)
ATGGATTCACAGGCCCAGGTTCTTATGTTACTGCTGCTATGGGATTCTGGTACCTGTGGG
GACATTGTGATGTCACAGTCTCCATCCTCCCCTAGCTGTGTCAGTTGGAGAGAAGGTTACT
ATGAGCTGCAAGTCCAGTCAGAGCCTTTTATATAGTAGCAATCAAAAGAACTACTTGGCC
TGGTACCAGCAGAAACCAGGGCACTCTCCTAAACTGCTGATTTACTGGGCATCCACTAGG
GAATCTGGGGTCCCTGATCGCTTCACAGGCAGTGGATCTGGGACAGATTTCACTCTCACC
ATCAGCAGTGTGAAGGCTGAAGACCTGGCAGTTTATTACTGTCAGCAAAATTTTATCTAT
CCGCTCACGTTCGGTGCTGGGACCAAGCTGGAGCTGAAACGTGAGTTCTAGAGGATCCA
TCTGGGATAAGCATGCTGTTTTCTGTCTGTCCCTAACATGCCCTGTGATTATCCGCAAACA
ACACACCCAAGGGCAGAACTTTGTTACTTAAACACCATCCTGTTTGCTTCTTTCCTCAGG
AACTGTGGCTGCACCATCTGTCTTCATCTTCCCGCCATCTGATGAGCAGTTGAAATCTGG
AACTGCCTCTGTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAGAGCAGGACA
GCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAA
GAGCTTCAACAGGGGAGAGTGTTAG (SEQ ID NO: 21)

IMM4701's long chain (SIRPαD1-linker-IMM47's heavy chain)
EEELQVIQPDKSVSVAAGESAILHCTVTSLIPVGPIQWFRGAGPARELIYNQKEGHFPRVTTVS
ESTKRENMDFSISISAITPADAGTYYCVKFRKGSPDTEFKSGAGTELSVRAKPSAPVVSGPGG
GGSGGGGSGGGGSDVQLQESGPDLVKPSQSLSLTCTVTGYSITSGYSWHWIRQFPGNKLEW
MGYIHYSGSTKYNPSLKSRISITRDTSKNQFFLQLNSVTTEDTATYFCARGADYALDYWGQR
TSVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQYN
ATYRVVSVLTVLHQDWLNGKEYKCKVSNKALPAPIAATISKAKGQPREPQVYTLPPSREEMT
KNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 18)

IMM4701's short chain (IMM47's light chain)
DIQMTQSPSSLSASVGDRVTITCKSSQSLLYSSNQKNYLAWYQQKPGKAPKLLIYWASTRES
GVPSRFSGSGSGTDFTLTISSLQPEDFATYYCQQNFIYPLTFGGGTKVELKRTVAAPSVFIFPPS
DEQLKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 22)
ATGGGATGGTCATGTATCATCCTTTTTCTGGTAGCAACTGCAACTGGAGTACATTCAGAC
ATTCAGATGACACAGAGCCCTAGCAGCCTGAGCGCCTCCGTGGGCGACAGAGTGACCAT
CACCTGCAAGAGCAGCCAAAGCCTGCTGTACAGCAGCAATCAGAAGAACTACCTGGCCT
GGTATCAGCAGAAGCCTGGCAAGGCCCCTAAGCTGCTGATCTACTGGGCCTCCACAAGA
GAGAGCGGCGTGCCTAGCAGATTCAGCGGCAGCGGCAGCGGCACCGACTTCACCCTGAC
CATCAGCAGCCTGCAGCCTGAGGACTTCGCCACCTACTACTGTCAGCAGAACTTCATCTA
CCCTCTGACCTTCGGCGGAGGCACCAAGGTGGAGCTGAAGCGTGAGTTCTAGAGGATCC
ATCTGGGATAAGCATGCTGTTTTCTGTCTGTCCCTAACATGCCCTGTGATTATCCGCAAAC
AACACACCCAAGGGCAGAACTTTGTTACTTAAACACCATCCTGTTTGCTTCTTTCCTCAG

| Description<br>Sequence/SEQ ID NO. |
|---|
| GAACTGTGGCTGCACCATCTGTCTTCATCTTCCCGCCATCTGATGAGCAGTTGAAATCTG<br>GAACTGCCTCTGTTGTGTGCCTGCTGAATAACTTCTATCCCAGAGAGGCCAAAGTACAGT<br>GGAAGGTGGATAACGCCCTCCAATCGGGTAACTCCCAGGAGAGTGTCACAGAGCAGGAC<br>AGCAAGGACAGCACCTACAGCCTCAGCAGCACCCTGACGCTGAGCAAAGCAGACTACGA<br>GAAACACAAAGTCTACGCCTGCGAAGTCACCCATCAGGGCCTGAGCTCGCCCGTCACAA<br>AGAGCTTCAACAGGGGAGAGTGTTAG (SEQ ID NO: 23) |
| IMM4702C's long chain (IMM47C's heavy chain)<br>DVQLQESGPDLVKPSQSLSLTCTVTGYSITSGYSWHWIRQFPGNKLEWMGYIHYSGSTKYNP<br>SLKSRISITRDTSKNQFFLQLNSVTTEDTATYFCARGADYALDYWGQRTSVTVSSASTKGPSV<br>FPLAPSSKSTSGGTAALGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPELLGGPSVFLFPPKPKDTL<br>MISRTPEVTCVVVDVSHEDPEVKFNWYVDGVEVHNAKTKPREEQYNATYRVVSVLTVLHQ<br>DWLNGKEYKCKVSNKALPAPIAATISKAKGQPREPQVYTLPPSREEMTKNQVSLTCLVKGFY<br>PSDIAVEWESNGQPENNYKTTPPVLDSDGSFFLYSKLTVDKSRWQQGNVFSCSVMHEALHN<br>HYTQKSLSLSPGK (SEQ ID NO: 24) |
| ATGAGAGTGCTGATTCTTTTGTGCCTGTTCACAGCCTTTCCTGGTATCCTGTCTGATGTGC<br>AGCTTCAGGAGTCAGGACCTGACCTGGTGAAACCTTCTCAGTCACTTTCACTCACCTGCA<br>CTGTCACTGGCTACTCCATCACCAGTGGTTATAGCTGGCACTGGATCCGGCAGTTTCCAG<br>GAAACAAACTGGAATGGATGGCTACATACACTATAGTGGTAGCACTAAGTACAACCCA<br>TCTCTCAAAAGTCGAATCTATCACTCGAGACACATCCAAGAACCAGTTCTTCCTGCAG<br>TTGAATTCTGTGACTACTGAGGACACAGCCACATATTTCTGTGCAAGAGGCGCGGACTAT<br>GCTTTGGACTACTGGGGTCAACGAACCTCAGTCACCGTCTCCTCAGCTAGCACCAAGGGC<br>CCATCGGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAGGCGC<br>CCTGACCAGCGGCGTGCACACCTTCCCGGCTGTCCTACAGTCCTCAGGACTCTACTCCCT<br>CAGCAGCGTGGTGACCGTGCCCTCCAGCAGCTTGGGCACCCAGACCTACATCTGCAACGT<br>GAATCACAAGCCCAGCAACACCAAGGTGGACAAGAGAGTTGAGCCCAAATCTTGTGACA<br>AAACTCACACATGCCCACCGTGCCCAGCACCTGAACTCCTGGGGGGACCGTCAGTCTTCC<br>TCTTCCCCCCAAAACCCAAGGACACCCTCATGATCTCCCGGACCCCTGAGGTCACATGCG<br>TGGTGGTGGACGTGAGCCACGAAGACCCTGAGGTCAAGTTCAACTGGTATGTGGACGGC<br>GTGGAGGTGCATAATGCCAAGACAAAGCCGCGGGAGGAGCAGTACAACGCCACGTACC<br>GTGTGGTCAGCGTCCTCACCGTCCTGCACCAAGACTGGCTGAATGGCAAGGAGTACAAG<br>TGCAAGGTCTCCAACAAAGCCCTCCCAGCCCCCATCGCCGCAACCATCTCCAAAGCCAA<br>AGGGCAGCCCCGAGAACCACAGGTGTACACCCTGCCCCCATCCCGGGAGGAGATGACCA<br>AGAACCAAGTCAGCCTGACCTGCCTGGTCAAAGGCTTCTATCCCAGCGACATCGCCGTGG<br>AGTGGGAGAGCAATGGGCAGCCGGAGAACAACTACAAGACCACGCCTCCCGTGCTGGAC<br>TCCGACGGCTCCTTCTTCCTCTATTCCAAGCTCACCGTGGACAAGAGCAGGTGGCAGCAG<br>GGGAACGTCTTCTCATGCTCCGTGATGCATGAGGCTCTGCACAACCACTACACGCAGAAG<br>AGCCTCTCCCTGTCTCCGGGCAAATGA (SEQ ID NO: 25) |
| IMM4702C's short chain (SIRPαD1-linker-IMM47C's light chain)<br>EEELQVIQPDKSVSVAAGESAILHCTVTSLIPVGPIQWFRGAGPARELIYNQKEGHFPRVTTVS<br>ESTKRENMDFSISISAITPADAGTYYCVKFRKGSPDTEFKSGAGTELSVRAKPSAPVVSGPGG<br>GGSGGGGSGGGGSDIVMSQSPSSLAVSVGEKVTMSCKSSQSLLYSSNQKNYLAWYQQKPGH<br>SPKLLIYWASTRESGVPDRFTGSGSGTDFTLTISSVKAEDLAVYYCQQNFIYPLTFGAGTKLEL<br>KRTVAAPSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 26) |
| ATGGGATGGTCATGTATCATCCTTTTTCTGGTAGCAACTGCAACTGGAGTACATTCAGAG<br>GAGGAGCTGCAGGTGATTCAGCCTGACAAGTCCGTATCAGTTGCAGCTGGAGAGTCGGC<br>CATTCTGCACTGCACTGTGACCTCCCTGATCCCTGTGGGGCCCATCCAGTGGTTCAGAGG<br>AGCTGGACCAGCCCGGGAATTAATCTACAATCAAAAGAAGGCCACTTCCCCCGGGTAA<br>CAACTGTTTCAGAGTCCACAAAGAGAGAAAACATGGACTTTTCCATCAGCATCAGTGCC<br>ATCACCCCAGCAGATGCCGGCACCTACTACTGTGTGAAGTTCCGGAAAGGGAGCCCTGA<br>CACGGAGTTTAAGTCTGGAGCAGGCACTGAGCTGTCTGTGCGTGCCAAACCCTCTGCCCC<br>CGTGGTATCGGGCCCTGGCGGCGGTGGGAGCGGCGGCGGTGGGAGCGGCGGCGGGGC<br>TCGGACATTGTGATGTCACAGTCTCCATCCTCCCTAGCTGTGTCAGTTGGAGAGAAGGTT<br>ACTATGAGCTGCAAGTCCAGTCAGAGCCTTTTATATAGTAGCAATCAAAAGAACTACTTG<br>GCCTGGTACCAGCAGAAACCAGGGCACTCTCCTAAACTGCTGATTTACTGGGCATCCACT<br>AGGGAATCTGGGGTCCCTGATCGCTTCACAGGCAGTGGATCTGGGACAGATTTCACTCTC<br>ACCATCAGCAGTGTGAAGGCTGAAGACCTGGCAGTTTATTACTGTCAGCAAAATTTTATC<br>TATCCGCTCACGTTCGGTGCTGGGACCAAGCTGGAGCTGAAGCGTGAGTTCTAGAGGATC<br>CATCTGGGATAAGCATGCTGTTTTCTGTCTGTCCCTAACATGCCCTGTGATTATCCGCAAA<br>CAACACACCCAAGGGCAGAACTTTGTTACTTAAACACCATCCTGTTTGCTTCTTTCCTCAG<br>GAACTGTGGCTGCACCATCTGTCTTCATCTTCCCGCCATCTGATGAGCAGTTGAAATCTG<br>GAACTGCCTCTGTTGTGTGCCTGCTGAATAACTTCTATCCCAGAGAGGCCAAAGTACAGT<br>GGAAGGTGGATAACGCCCTCCAATCGGGTAACTCCCAGGAGAGTGTCACAGAGCAGGAC<br>AGCAAGGACAGCACCTACAGCCTCAGCAGCACCCTGACGCTGAGCAAAGCAGACTACGA<br>GAAACACAAAGTCTACGCCTGCGAAGTCACCCATCAGGGCCTGAGCTCGCCCGTCACAA<br>AGAGCTTCAACAGGGGAGAGTGTTAG (SEQ ID NO: 27) |
| IMM4702H's long chain (IMM47H's heavy chain)<br>DVQLQESGPGLVKPSETLSLTCTVSGYSITSGYSWHWIRQPPGKGLEWIGYIHYSGSTKYNPS<br>LKSRVTISVDTSKNQFSLKLSSVTAADTAVYYCARGADYALDYWGQRTSVTVSSASTKGPSV<br>FPLAPSSKSTSGGTAALGCLVKDYFPEPVTVSWNSGALTSGVHTFPAVLQSSGLYSLSSVVTV<br>PSSSLGTQTYICNVNHKPSNTKVDKRVEPKSCDKTHTCPPCPAPELLGGPSVFLFPPKPKDTL |

| Description |
|---|
| Sequence/SEQ ID NO. |

MISRTPEVTCVVVDVSHEDPEVKFNWYVDGVEVHNAKTKPREEQYNATYRVVSVLTVLHQ
DWLNGKEYKCKVSNKALPAPIAATISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHN
HYTQKSLSLSPGK (SEQ ID NO: 28)
ATGGGATGGTCATGTATCATCCTTTTTCTGGTAGCAACTGCAACTGGAGTACATTCAGAC
GTGCAGCTGCAAGAGAGCGGCCCTGGCCTGGTGAAGCCTAGCGAGACCCTGAGCCTGAC
CTGCACCGTGTCCGGCTACAGCATCACAAGCGGCTACAGCTGGCACTGGATCAGACAGC
CTCCTGGCAAGGGCCTGGAGTGGATCGGCTACATCCACTACAGCGGCAGCACCAAGTAC
AACCCTAGCCTGAAGAGCAGAGTGACCATCAGCGTGGACACAAGCAAGAATCAGTTCAG
CCTGAAGCTGAGCAGCGTGACCGCCGCCGACACCGCCGTGTACTACTGCGCTAGAGGCG
CCGACTACGCCCTGGACTACTGGGGACAGAGAACAAGCGTGACCGTGAGCAGCGCTAGC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAGAGTTGAGCCCAAAT
CTTGTGACAAAACTCACACATGCCCACCGTGCCCAGCACCTGAACTCCTGGGGGGACCGT
CAGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTAT
GTGGACGGCGTGGAGGTGCATAATGCCAAGACAAAGCCGCGGGAGGAGCAGTACAACG
CCACGTACCGTGTGGTCAGCGTCCTCACCGTCCTGCACCAAGACTGGCTGAATGGCAAGG
AGTACAAGTGCAAGGTCTCCAACAAAGCCCTCCCAGCCCCCATCGCCGCAACCATCTCCA
AAGCCAAAGGGCAGCCCCGAGAACCACAGGTGTACACCCTGCCCCCATCCCGGGAGGAG
ATGACCAAGAACCAAGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGT
GCTGGACTCCGACGGCTCCTTCTTCCTCTATTCCAAGCTCACCGTGGACAAGAGCAGGTG
GCAGCAGGGGAACGTCTTCTCATGCTCCGTGATGCATGAGGCTCTGCACAACCACTACAC
GCAGAAGAGCCTCTCCCTGTCTCCGGGCAAATGA (SEQ ID NO: 29)

IMM4702H's short chain (SIRPαD1-linker-IMM47H's light chain)
EEELQVIQPDKSVSVAAGESAILHCTVTSLIPVGPIQWFRGAGPARELIYNQKEGHFPRVTTVS
ESTKRENMDFSISISAITPADAGTYYCVKFRKGSPDTEFKSGAGTELSVRAKPSAPVVSGPGG
GGSGGGGSGGGGSDIVMTQSPDSLAVSLGERATINCKSSQSLLYSSNQKNYLAWYQQKPGQ
PPKLLIYWASTRESGVPDRFSGSGSGTDFTLTISSLQAEDVAVYYCQQNFIYPLTFGGGTKVEL
KRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC (SEQ ID NO: 30)
ATGGGATGGTCATGTATCATCCTTTTTCTGGTAGCAACTGCAACTGGAGTACATTCAGAG
GAGGAGCTGCAGGTGATTCAGCCTGACAAGTCCGTATCAGTTGCAGCTGGAGAGTCGGC
CATTCTGCACTGCACTGTGACCTCCCTGATCCCTGTGGGGCCCATCCAGTGGTTCAGAGG
AGCTGGACCAGCCCGGGAATTAATCTACAATCAAAAAGAAGGCCACTTCCCCCGGGTAA
CAACTGTTTCAGAGTCCACAAAGAGAGAAAACATGGACTTTTCCATCAGCATCAGTGCC
ATCACCCCCAGCAGATGCCGGCACCTACTACTGTGTGAAGTTCCGGAAAGGGAGCCCTGA
CACGGAGTTTAAGTCTGGAGCAGGCACTGAGCTGTCTGTGCGTGCCAAACCCTCTGCCCC
CGTGGTATCGGGCCCTGGCGGCGGTGGGAGCGGCGGCGGTGGGAGCGGCGGCGGGGGC
TCGGACATCGTGATGACACAGAGCCCTGACAGCCTGGCCGTGAGCCTGGGCGAGAGAGC
CACCATCAACTGCAAGAGCTCTCAGAGCCTGCTGTACAGCAGCAATCAGAAGAACTACC
TGGCCTGGTATCAGCAGAAGCCTGGACAGCCTCCTAAGCTGCTGATCTACTGGGCAAGC
ACAAGAGAGAGCGGCGTGCCTGACAGATTCAGCGGCAGCGGCAGCGGCACCGACTTCAC
CCTGACCATCAGCAGCCTGCAAGCCGAGGACGTGGCCGTGTACTACTGTCAGCAGAACT
TCATCTACCCTCTGACCTTCGGCGGCGGCACCAAGGTGGAGCTGAAGCGTGAGTTCTAGA
GGATCCATCTGGGATAAGCATGCTGTTTTCTGTCTGTCCCTAACATGCCCTGTGATTATCC
GCAAACAACACACCCAAGGGCAGAACTTTGTTACTTAAACACCATCCTGTTTGCTTCTTT
CCTCAGGAACTGTGGCTGCACCATCTGTCTTCATCTTCCCGCCATCTGATGAGCAGTTGA
AATCTGGAACTGCCTCTGTTGTGTGCCTGCTGAATAACTTCTATCCCAGAGAGGCCAAAG
TACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGCAG
ACTACGAGAAACACAAAGTCTACGCCTGCGAAGTCACCCATCAGGGCCTGAGCTCGCCC
GTCACAAAGAGCTTCAACAGGGGAGAGTGTTAG (SEQ ID NO: 31)

SIRPαD1 mutant-Fc (IMM01)
EEELQVIQPDKSVSVAAGESAILHCTVTSLIPVGPIQWFRGAGPARELIYNQKEGHFPRVTTVS
ESTKRENMDFSISISAITPADAGTYYCVKFRKGSPDTEFKSGAGTELSVRAKPSAPVVSGPAAR
ATPQHEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG (SEQ ID NO: 32)
GAGGAGGAGCTGCAGGTGATTCAGCCTGACAAGTCCGTATCAGTTGCAGCTGGAGAGTC
GGCCATTCTGCACTGCACTGTGACCTCCCTGATCCCTGTGGGGCCCATCCAGTGGTTCAG
AGGAGCTGGACCAGCCCGGGAATTAATCTACAATCAAAAAGAAGGCCACTTCCCCCGGG
TAACAACTGTTTCAGAGTCCACAAAGAGAGAAAACATGGACTTTTCCATCAGCATCAGT
GCCATCACCCCCAGCAGATGCCGGCACCTACTACTGTGTGAAGTTCCGGAAAGGGAGCCC
TGACACGGAGTTTAAGTCTGGAGCAGGCACTGAGCTGTCTGTGCGTGCCAAACCCTCTGC
CCCCGTGGTATCGGGCCCTGCGGCGAGGGCCACACCTCAGCACGAGCCCAAATCTTGTG
ACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGA

| Description Sequence/SEQ ID NO. |
|---|
| CGGCGTGGAGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGGCAAGGAGTAC<br>AAGTGCAAGGTCTCCAACAAAGCCCTCCCAGCCCCCATCGAGAAAACCATCTCCAAAGC<br>CAAAGGGCAGCCCCGAGAACCACAGGTGTACACCCTGCCCCCATCCCGGGATGAGCTGA<br>CCAAGAACCAGGTCAGCCTGACCTGCCTGGTCAAAGGCTTCTATCCCAGCGACATCGCCG<br>TGGAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCACTACACGCAG<br>AAGAGCCTCTCCCTGTCTCCGGGTTGA (SEQ ID NO: 33)<br><br>nucleotide encoding mouse IgG1 heavy chain signal peptide<br>ATGGGATGGTCATGTATCATCCTTTTTCTGGTAGCAACTGCAACTGGAGTACATTCA (SEQ ID NO: 34)<br><br>Kozak consensus sequence<br>GCCGCCACC (SEQ ID NO: 35)<br><br>human SIRPα-mouse IgG1 Fc<br>MGWSCIILFLVATATGVHSSCAWSGVAGEEELQVIQPDKSVSVAAGESAILHCTVTSLIPVGPI<br>QWFRGAGPARELIYNQKEGHFPRVTTVSESTKRENMDFSISISNITPADAGTYYCVKFRKGSP<br>DTEFKSGAGTELSVRAKPSAPVVSGPAARATPQHTVSFTCESHGFSPRDITLKWFKNGNELSD<br>FQTNVDPVGESVSYSIHSTAKVVLTREDVHSQVICEVAHVTLQGDPLRGTANLSETIRVPPTL<br>EVTQQPVRAENQVNVTCQVRKFYPQRLQLTWLENGNVSRTETASTVTENKDGTYNWMSWL<br>LVNVSAHRDDVKLTCQVEHDGQPAVSKSHDLKVSAHPKEQGSNTAAENTGSNERNEFVPRD<br>CGCKPCICTVPEVSSVFIFPPKPKDVLTITLTPKVTCVVVDISKDDPEVQFSWFVDDVEHTAQ<br>TQPREEQFNSTFRSVSELPIMHQDWLNGKEFKCRVNSAAFPAPIEKTISKTKGRPKAPQVYTIP<br>PPKEQMAKDKVSLTCMITDFFPEDITVEWQWNGQPAENYKNTQPIMNTNGSYFVYSKLNVQ<br>KSNWEAGNTFTCSVLHEGLHNHHTEKSLSHSPGK (SEQ ID NO: 36) |

While the application has been described above in connection with one or more embodiments, it should be understood that the application is not limited to those embodiments, and the description is intended to cover all alternatives, modifications, and equivalents, as may be included within the spirit and scope of the appended claims. All referenced cited herein are further incorporated by reference in their entirety.

REFERENCES

1. Barkal, A. A., Brewer, R. E., Markovic, M., Kowarsky, M., Barkal, S. A., Zaro, B. W., Krishnan, V., Hatakeyama, J., Dorigo, O., Barkal, L. J., et al. (2019). CD24 signalling through macrophage Siglec-10 is a target for cancer immunotherapy. Nature 572(7769), 392-396
2. Chan, S. H., Tsai, K. W., Chiu, S. Y., Kuo, W. H., Chen, H. Y., Jiang, S. S., Chang, K. J., Hung, W. C., and Wang, L. H. (2019). Identification of the Novel Role of CD24 as an Oncogenesis Regulator and Therapeutic Target for Triple-Negative Breast Cancer. Mol Cancer Ther 18(1), 147-161
3. Wang S, Chen K, Lei Q, Ma P, Yuan A Q, Zhao Y, Jiang Y, Fang H, Xing S, Fang Y, Jiang N, Miao H, Zhang M, Sun S, Yu Z, Tao W, Zhu Q, Nie Y, Li N. The state of the art of bispecific antibodies for treating human malignancies. EMBO Mol Med. 2021 Aug. 24:e14291. doi: 10.15252/emmm.202114291
4. Yin, S. S., and Gao, F. H. (2020). Molecular Mechanism of Tumor Cell Immune Escape Mediated by CD24/Siglec-10. Front Immunol 11, 1324
5. Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334
6. Gennaro, ed., Remington: The Science and Practice of Pharmacy, 20th Ed., Lippincott Williams & Wilkins 2003
7. J. R. Robinson, ed., Sustained and Controlled Release Drug Delivery Systems, Marcel Dekker, Inc., New York, 1978
8. Lee W Y, Weber D A, Laur O, Severson E A, McCall I, Jen R P, Chin A C, Wu T, Gernert K M, Parkos C A. Novel Structural Determinants on SIRPa that Mediate Binding to CD47. J Immunol. 2007, 179:7741-7750
9. Liu, C., Zheng, S., Shen, H., Xu, K., Chen, J., Li, H., Xu, Y., Xu, A., Chen, B., Kaku, H., et al. (2013). Clinical significance of CD24 as a predictor of bladder cancer recurrence. Oncol Lett 6(1), 96-100
10. Nakamura et al. CD24 expression is a marker for predicting clinical outcome and regulates the epithelial-mesenchymal transition in ovarian cancer via both the Akt and ERK pathways. Oncol Rep. 2017 June; 37(6):3189-3200
11. Obeid M, Panaretakis T, Joza N, Tufi R, Tesniere A, van Endert P, Zitvogel L, Kroemer G. Calreticulin exposure is required for the immunogenicity of gamma-irradiation and UVC lightinduced apoptosis. Cell Death Differ. 2007, 14:1848-1850
12. Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003, 161:1179-1189
13. Overdevest, J. B., Thomas, S., Kristiansen, G., Hansel, D. E., Smith, S. C., and Theodorescu, D. (2011). CD24 offers a therapeutic target for control of bladder cancer metastasis based on a requirement for lung colonization. Cancer Res 71(11), 3802-11
14. Shields R L, Namenuk A K, Hong K, Meng Y G, Rae J, Briggs J, Xie D, Lai J, Stadlen A, Li B, Fox J A, Presta L G. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604

15. Shim H. Bispecific Antibodies and Antibody-Drug Conjugates for Cancer Therapy: Technological Considerations. Biomolecules. 2020 Feb. 26; 10(3):360
16. Theocharides, A. P. A.; Jin, L. Q.; Cheng, P. Y.; Prasolava, T. K.; Malko, A. V.; Ho, J. M.; Poeppl, A. G.; Rooijen, N. van; Minden, M. D.; Danska, J. S.; Dick, J.; Wang, J. C. Y. J. Exp. Med. 2012, Vol. 209 No. 10 1883-1899
17. Tseng D, Volkmer J P, Willingham S B, Contreras-Trujillo H, Fathman J W, Fernhoff N B, Seita J, Inlay M A, Weiskopf K, Miyanishi M, Weissman I L. Anti-CD47 antibody-mediated phagocytosis of cancer by macrophages primes an effective antitumor T-cell response. PNAS. 2013, 110:11103-11108
18. Wu H, Liu J, Wang Z, Yuan W, Chen L. Prospects of antibodies targeting CD47 or CD24 in the treatment of glioblastoma. CNS Neurosci Ther. 2021 October; 27(10): 1105-1117. doi: 10.1111/cns.13714. Epub 2021 Aug. 6. PMID: 34363319; PMCID: PMC8446212

The invention claimed is:

1. A recombinant fusion protein, comprising an anti-CD24 antibody or an antibody fragment thereof, and a CD47 binding peptide,
wherein the anti-CD24 antibody or antibody fragment thereof comprises a heavy chain variable region, a heavy chain constant region, and a light chain variable region, wherein the heavy chain variable region comprises a heavy chain variable CDR-1 (HV-CDR1), a HV-CDR2 and a HV-CDR3 having amino acid sequences set forth in SEQ ID NOs: 7, 8 and 9, respectively, the light chain variable region comprises a light chain variable CDR-1 (LV-CDR1), a LV-CDR2 and a LV-CDR3 having amino acid sequences set forth in SEQ ID NOs: 10, 11 and 12, respectively, and the heavy chain constant region has Fc binding affinity and is linked to C-terminus of the heavy chain variable region,
wherein the CD47 binding peptide comprises a signal-regulatory protein (SIRP) extracellular domain having an amino acid sequence having at least 95% sequence identity to SEQ ID NO: 1,
wherein the CD47 binding peptide is linked to the anti-CD24 antibody or antibody fragment thereof.

2. The recombinant fusion protein of claim 1, wherein at least one paratope of the anti-CD24 antibody or antibody fragment thereof is linked to the CD47 binding peptide at N-terminus of the heavy chain variable region or the light chain variable region constituting the paratope.

3. The recombinant fusion protein of claim 2, wherein each paratope of the anti-CD24 antibody or antibody fragment thereof is linked to the CD47 binding peptide at N-terminus of the heavy chain variable region or the light chain variable region constituting the paratope.

4. The recombinant fusion protein of claim 3, wherein each paratope of the anti-CD24 antibody or antibody fragment thereof is linked to the CD47 binding peptide at N-terminus of the heavy chain variable region constituting the paratope.

5. The recombinant fusion protein of claim 3, wherein each paratope of the anti-CD24 antibody or antibody fragment thereof is linked to the CD47 binding peptide at N-terminus of the light chain variable region constituting the paratope.

6. The recombinant fusion protein of claim 1, wherein the heavy chain variable region and the light chain variable region comprise amino acid sequences of i) SEQ ID NOs: 2 and 3, respectively; ii) SEQ ID NOs: 2 and 4, respectively; or iii) SEQ ID NOs: 5 and 6, respectively.

7. The recombinant fusion protein of claim 1, wherein the heavy chain constant region comprises the amino acid sequence of SEQ ID NO: 13.

8. The recombinant fusion protein of claim 1, further comprising a light chain constant region having the amino acid sequence of SEQ ID NO: 14, linked to the C-terminus of the light chain variable region.

9. The recombinant fusion protein of claim 3, wherein the anti-CD24 antibody or antibody fragment thereof is linked to the CD47 binding peptide via a linker.

10. The recombinant fusion protein of claim 9, wherein the linker is -(Gly-Gly-Gly-Gly-Ser)₃-(SEQ ID NO: 15), -(Gly-Gly-Gly-Gly-Ser)₂-(SEQ ID NO: 16), or -(Gly-Gly-Gly-Gly-Ser)₄-(SEQ ID NO: 17).

11. The recombinant fusion protein of claim 9, comprising
i) a CD47 binding peptide-linker-anti-CD24 heavy chain variable region-heavy chain constant region fragment having the amino acid sequence of SEQ ID NO: 18, and an anti-CD24 light chain variable region-light chain constant region fragment having the amino acid sequence of SEQ ID NO: 20;

ii) a CD47 binding peptide-linker-anti-CD24 heavy chain variable region-heavy chain constant region fragment having the amino acid sequence of SEQ ID NO: 18, and an anti-CD24 light chain variable region-light chain constant region fragment having the amino acid sequence of SEQ ID NO: 22;

iii) an anti-CD24 heavy chain variable region-heavy chain constant region fragment having the amino acid sequence of SEQ ID NO: 24, and a CD47 binding peptide-linker-anti-CD24 light chain variable region-light chain constant region fragment having the amino acid sequence of SEQ ID NO: 26; or iv) an anti-CD24 heavy chain variable region-heavy chain constant region fragment having the amino acid sequence of SEQ ID NO: 28, and a CD47 binding peptide-linker-anti-CD24 light chain variable region-light chain constant region fragment having the amino acid sequence of SEQ ID NO: 30.

12. A nucleic acid molecule encoding the recombinant fusion protein of claim 1.

13. An expression vector comprising the nucleic acid molecule of claim 12.

14. A host cell comprising the expression vector of claim 13.

15. A pharmaceutical composition, comprising the recombinant fusion protein of claim 1, and at least one pharmaceutically acceptable excipient.

16. The pharmaceutical composition of claim 15, further comprising at least one pharmaceutically acceptable adjuvant.

17. A method for treating a disease associated with over-expression of CD47 and/or CD24 in a subject in need thereof, comprising administering to the subject the pharmaceutical composition of claim 15.

18. The method of claim 17, wherein the disease is selected from the group consisting of acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, renal cell carcinoma, cervical cancer, endometrial cancer, cholangiocarcinoma, stomach adenocarcinoma, and glioblastoma.

* * * * *